United States Patent
Al-Ali et al.

(10) Patent No.: US 10,813,598 B2
(45) Date of Patent: Oct. 27, 2020

(54) SYSTEM AND METHOD FOR MONITORING RESPIRATORY RATE MEASUREMENTS

(71) Applicant: MASIMO CORPORATION, Irvine, CA (US)

(72) Inventors: Ammar Al-Ali, San Juan Capistrano, CA (US); Bilal Muhsin, San Clemente, CA (US); Michael O'Reilly, San Jose, CA (US)

(73) Assignee: MASIMO CORPORATION, Irvine, CA (US)

( * ) Notice: Subject to any disclaimer, the term of this patent is extended or adjusted under 35 U.S.C. 154(b) by 488 days.

(21) Appl. No.: 15/851,176

(22) Filed: Dec. 21, 2017

(65) Prior Publication Data

US 2018/0214090 A1    Aug. 2, 2018

Related U.S. Application Data

(63) Continuation of application No. 14/752,466, filed on Jun. 26, 2015, now Pat. No. 9,877,686, which is a
(Continued)

(51) Int. Cl.
*A61B 5/08* (2006.01)
*A61B 5/0205* (2006.01)
(Continued)

(52) U.S. Cl.
CPC ............ *A61B 5/746* (2013.01); *A61B 5/0205* (2013.01); *A61B 5/02416* (2013.01);
(Continued)

(58) Field of Classification Search
CPC ... A61B 5/746; A61B 5/0205; A61B 5/02416; A61B 5/0402; A61B 5/0803;
(Continued)

(56) References Cited

U.S. PATENT DOCUMENTS 3,682,161 A    8/1972  Alibert
4,127,749 A    11/1978 Atoji et al.
(Continued)

FOREIGN PATENT DOCUMENTS

CA    2262236    4/2008
EP    0716628    12/1998
(Continued)

OTHER PUBLICATIONS

US 8,845,543 B2, 09/2014, Diab et al. (withdrawn)
(Continued)

*Primary Examiner* — Navin Natnithithadha
(74) *Attorney, Agent, or Firm* — Knobbe, Martens, Olson & Bear LLP

(57) ABSTRACT

This disclosure describes, among other features, systems and methods for using multiple physiological parameter inputs to determine multiparameter confidence in respiratory rate measurements. For example, a patient monitoring system can programmatically determine multiparameter confidence in respiratory rate measurements obtained from an acoustic sensor based at least partly on inputs obtained from other non-acoustic sensors or monitors. The patient monitoring system can output a multiparameter confidence indication reflective of the programmatically-determined multiparameter confidence. The multiparameter confidence indication can assist a clinician in determining whether or how to treat a patient based on the patient's respiratory rate.

20 Claims, 22 Drawing Sheets

Related U.S. Application Data continuation of application No. 12/905,449, filed on Oct. 15, 2010, now Pat. No. 9,066,680.

(60) Provisional application No. 61/252,086, filed on Oct. 15, 2009, provisional application No. 61/261,199, filed on Nov. 13, 2009, provisional application No. 61/366,866, filed on Jul. 22, 2010.

(51) Int. Cl.

| | | |
|---|---|---|
| *A61B 5/024* | (2006.01) | |
| *A61B 5/021* | (2006.01) | |
| *A61B 5/044* | (2006.01) | |
| *G16H 40/63* | (2018.01) | |
| *G16H 40/67* | (2018.01) | |
| *A61B 5/00* | (2006.01) | |
| *G06F 19/00* | (2018.01) | |
| *A61B 5/1455* | (2006.01) | |
| *A61B 5/0402* | (2006.01) | |
| *A61B 7/00* | (2006.01) | |
| *A61B 5/145* | (2006.01) | |

(52) U.S. Cl.
CPC .......... *A61B 5/0402* (2013.01); *A61B 5/0803* (2013.01); *A61B 5/0816* (2013.01); *A61B 5/14551* (2013.01); *A61B 5/7221* (2013.01); *A61B 5/742* (2013.01); *A61B 7/003* (2013.01); *G06F 19/3418* (2013.01); *G16H 40/63* (2018.01); *G16H 40/67* (2018.01); *A61B 5/021* (2013.01); *A61B 5/024* (2013.01); *A61B 5/044* (2013.01); *A61B 5/14542* (2013.01); *A61B 5/7278* (2013.01)

(58) Field of Classification Search
CPC . A61B 5/0816; A61B 5/14551; A61B 5/7221; A61B 5/742; A61B 7/003; A61B 5/021; A61B 5/024; A61B 5/044; A61B 5/14542; A61B 5/7278; G16H 40/67; G16H 40/63; G06F 19/3418
USPC ....... 600/323, 324, 325, 326, 327, 328, 481, 600/483, 484, 500–503, 529, 538
See application file for complete search history.

(56) References Cited

U.S. PATENT DOCUMENTS

| | | |
|---|---|---|
| 4,326,143 A | 4/1982 | Guth et al. |
| 4,507,653 A | 3/1985 | Bayer |
| 4,537,200 A | 8/1985 | Widrow |
| 4,714,341 A | 12/1987 | Hamaguri |
| 4,848,901 A | 7/1989 | Hood, Jr. |
| 4,884,809 A | 12/1989 | Rowan |
| 4,958,638 A | 9/1990 | Sharpe et al. |
| 4,960,128 A | 10/1990 | Gordon et al. |
| 4,964,408 A | 10/1990 | Hink et al. |
| 5,033,032 A | 7/1991 | Houghtaling |
| 5,041,187 A | 8/1991 | Hink et al. |
| 5,069,213 A | 12/1991 | Polczynski |
| 5,143,078 A | 9/1992 | Mather et al. |
| 5,163,438 A | 11/1992 | Gordon et al. |
| 5,273,036 A | 12/1993 | Kronberg et al. |
| 5,309,922 A | 5/1994 | Schechter et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,302 A | 12/1994 | Tsiang |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,448,996 A | 9/1995 | Bellin et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,403 A | 6/1997 | Birchler et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,191 A | 9/1997 | Gerdt |
| 5,685,299 A | 11/1997 | Diab et al. |
| 5,724,983 A | 3/1998 | Selker et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,819,007 A | 10/1998 | Elghazzawi |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,865,736 A | 2/1999 | Baker, Jr. et al. |
| 5,890,929 A | 4/1999 | Mills et al. |
| 5,904,654 A | 5/1999 | Wohltmann et al. |
| 5,919,134 A | 7/1999 | Diab |
| 5,928,156 A | 7/1999 | Krumbiegel |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,029,665 A | 2/2000 | Berthon-Jones |
| 6,036,642 A | 3/2000 | Diab et al. |
| 6,045,509 A | 4/2000 | Caro et al. |
| 6,064,910 A | 5/2000 | Andersson et al. |
| 6,067,462 A | 5/2000 | Diab et al. |
| 6,081,735 A | 6/2000 | Diab et al. |
| 6,083,172 A | 7/2000 | Baker et al. |
| 6,088,607 A | 7/2000 | Diab et al. |
| 6,091,973 A | 7/2000 | Colla et al. |
| 6,110,522 A | 8/2000 | Lepper, Jr. et al. |
| 6,112,171 A | 8/2000 | Sugiyama et al. |
| 6,124,597 A | 9/2000 | Shehada |
| 6,128,521 A | 10/2000 | Marro et al. |
| 6,129,675 A | 10/2000 | Jay |
| 6,138,675 A | 10/2000 | Berthon-Jones |
| 6,139,505 A | 10/2000 | Murphy |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,168,568 B1 | 1/2001 | Gavriely |
| 6,178,343 B1 | 1/2001 | Bindszus et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |

(56) References Cited

U.S. PATENT DOCUMENTS

| | | |
|---|---|---|
| 6,248,083 B1 | 6/2001 | Smith et al. |
| 6,253,097 B1 | 6/2001 | Aronow et al. |
| 6,254,551 B1 | 7/2001 | Varis |
| 6,256,523 B1 | 7/2001 | Diab et al. |
| 6,261,238 B1 | 7/2001 | Gavriely |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,331,162 B1 | 12/2001 | Mitchell |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,383,143 B1 | 5/2002 | Rost |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,443,907 B1 | 9/2002 | Mansy et al. |
| 6,463,311 B1 | 10/2002 | Diab |
| 6,470,199 B1 | 10/2002 | Kopotic et al. |
| 6,486,588 B2 | 11/2002 | Doron et al. |
| 6,491,647 B1 | 12/2002 | Bridger et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,497 B2 | 2/2003 | Rymut et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,647,280 B2 | 11/2003 | Bahr et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,659,960 B2 | 12/2003 | Derksen et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,074 B1 | 4/2004 | Kastle |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,754,516 B2 | 6/2004 | Mannheimer |
| 6,760,607 B2 | 7/2004 | Al-Ali |
| 6,766,038 B1 | 7/2004 | Sakuma et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,839,581 B1 | 1/2005 | El-Solh et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,869,402 B2 | 3/2005 | Arnold |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,194,306 B1 | 3/2007 | Turcott |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,267,652 B2 | 9/2007 | Coyle et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,146 B1 | 4/2008 | Bharmi et al. |
| 7,371,981 B2 | 5/2008 | Abdul-Hafiz |

(56) References Cited

U.S. PATENT DOCUMENTS

| | | |
|---|---|---|
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,398,115 B2 | 7/2008 | Lynn |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,539,533 B2 | 5/2009 | Tran |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,690,378 B1 | 4/2010 | Turcott |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,478,538 B2 | 7/2013 | McGonigle et al. |
| 8,483,787 B2 | 7/2013 | Al-Ali et al. |

(56) References Cited

U.S. PATENT DOCUMENTS

| | | |
|---|---|---|
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,597,274 B2 | 12/2013 | Sloan |
| 8,600,467 B2 | 12/2013 | Al-Ali et al. |
| 8,606,342 B2 | 12/2013 | Diab |
| 8,622,902 B2 | 1/2014 | Woehrle |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,949 B2 | 7/2014 | Baker |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,135,398 B2 | 9/2015 | Kaib |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,220,440 B2 | 12/2015 | Addison et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 1/2016 | Abdul-Hafiz et al. |
| 9,267,572 B2 | 2/2016 | Barker et al. |
| 9,277,880 B2 | 2/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |

(56) References Cited

U.S. PATENT DOCUMENTS

| | | |
|---|---|---|
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,378,637 B2 | 6/2016 | Kaib |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,693 B2 | 4/2017 | Diab |
| 9,659,475 B2 | 5/2017 | Kaib |
| 9,724,016 B1 | 8/2017 | Al-Ali et al. |
| 9,848,800 B1 | 12/2017 | Lee |
| 9,877,686 B2 * | 1/2018 | Al-Ali ................ A61B 5/0816 |
| 9,968,266 B2 * | 5/2018 | An ..................... A61B 5/0205 |
| 2001/0002206 A1 | 5/2001 | Diab et al. |
| 2002/0193670 A1 | 12/2002 | Garfield et al. |
| 2003/0015368 A1 | 1/2003 | Cybulski et al. |
| 2003/0065269 A1 | 4/2003 | Vetter |
| 2003/0076494 A1 | 4/2003 | Bonin et al. |
| 2003/0158466 A1 | 8/2003 | Lynn et al. |
| 2003/0163033 A1 | 8/2003 | Dekker et al. |
| 2003/0163054 A1 | 8/2003 | Dekker |
| 2004/0010202 A1 | 1/2004 | Nakatani |
| 2004/0059203 A1 | 3/2004 | Guerrero |
| 2004/0133087 A1 | 7/2004 | Ali et al. |
| 2004/0158162 A1 | 8/2004 | Narimatsu |
| 2004/0225332 A1 | 11/2004 | Gebhardt |
| 2005/0027205 A1 | 2/2005 | Tarassenko et al. |
| 2005/0048456 A1 | 3/2005 | Chefd'hotel et al. |
| 2005/0070774 A1 | 3/2005 | Addison et al. |
| 2005/0107699 A1 | 5/2005 | Loftman |
| 2005/0116820 A1 | 6/2005 | Goldreich |
| 2005/0199056 A1 | 9/2005 | Strong |
| 2006/0047215 A1 | 3/2006 | Newman et al. |
| 2006/0149144 A1 | 7/2006 | Lynn et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0235324 A1 | 10/2006 | Lynn |
| 2006/0238333 A1 | 10/2006 | Welch et al. |
| 2006/0241510 A1 | 10/2006 | Halperin et al. |
| 2006/0258921 A1 | 11/2006 | Addison et al. |
| 2007/0093721 A1 | 4/2007 | Lynn et al. |
| 2007/0129643 A1 | 6/2007 | Kwok et al. |
| 2007/0129647 A1 | 6/2007 | Lynn |
| 2007/0135725 A1 | 6/2007 | Hatlestad |
| 2007/0149860 A1 | 6/2007 | Lynn et al. |
| 2007/0185397 A1 | 8/2007 | Govari et al. |
| 2007/0239057 A1 | 10/2007 | Pu et al. |
| 2007/0282212 A1 | 12/2007 | Sierra et al. |
| 2008/0013747 A1 | 1/2008 | Tran |
| 2008/0039735 A1 | 2/2008 | Hickerson |
| 2008/0071185 A1 | 3/2008 | Beck et al. |
| 2008/0076972 A1 | 3/2008 | Dorogusker et al. |
| 2008/0119716 A1 | 5/2008 | Boric-Lubecke et al. |
| 2008/0161878 A1 | 7/2008 | Tehrani et al. |
| 2008/0177195 A1 | 7/2008 | Armitstead |
| 2008/0188733 A1 | 8/2008 | Al-Ali |
| 2008/0188760 A1 | 8/2008 | Al-Ali |
| 2008/0218153 A1 | 9/2008 | Patel et al. |
| 2008/0275349 A1 | 11/2008 | Halperin et al. |
| 2008/0304580 A1 | 12/2008 | Ichiyama |
| 2009/0018409 A1 | 1/2009 | Banet et al. |
| 2009/0018429 A1 | 1/2009 | Saliga et al. |
| 2009/0018453 A1 | 1/2009 | Banet et al. |
| 2009/0093687 A1 | 4/2009 | Telfort et al. |
| 2009/0112096 A1 | 4/2009 | Tamura |
| 2009/0167332 A1 | 7/2009 | Forbes |
| 2009/0187065 A1 | 7/2009 | Basinger |
| 2009/0240119 A1 | 9/2009 | Schwaibold et al. |
| 2009/0247848 A1 | 10/2009 | Baker |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0004552 A1 | 1/2010 | Zhang et al. |
| 2010/0016682 A1 | 1/2010 | Schluess et al. |
| 2010/0016693 A1 | 1/2010 | Addison |
| 2010/0030040 A1 | 2/2010 | Poeze et al. |
| 2010/0204550 A1 | 8/2010 | Heneghan |
| 2010/0261979 A1 | 10/2010 | Kiani |
| 2010/0274099 A1 | 10/2010 | Telfort et al. |
| 2010/0295686 A1 | 11/2010 | Sloan |
| 2010/0298661 A1 | 11/2010 | McCombie et al. |
| 2010/0298730 A1 | 11/2010 | Tarassenko et al. |
| 2010/0324377 A1 | 12/2010 | Woehrle |
| 2011/0001605 A1 | 1/2011 | Kiani |
| 2011/0009710 A1 | 1/2011 | Kroeger et al. |
| 2011/0040713 A1 | 2/2011 | Colman |
| 2011/0066062 A1 | 3/2011 | Banet et al. |
| 2011/0074409 A1 | 3/2011 | Stoughton |
| 2011/0082711 A1 | 4/2011 | Poeze et al. |
| 2011/0105854 A1 | 5/2011 | Kiani et al. |
| 2011/0118573 A1 | 5/2011 | McKenna |
| 2011/0125060 A1 | 5/2011 | Telfort et al. |
| 2011/0172561 A1 | 7/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali et al. |
| 2011/0237911 A1 | 9/2011 | Lamego et al. |
| 2012/0016255 A1 | 1/2012 | Masuo |
| 2012/0059267 A1 | 3/2012 | Lamego et al. |
| 2012/0101344 A1 | 4/2012 | Desjardins |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0253140 A1 | 10/2012 | Addison et al. |
| 2012/0262298 A1 | 10/2012 | Bohm |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0045685 A1 | 2/2013 | Kiani |
| 2013/0046204 A1 | 2/2013 | Lamego |
| 2013/0041591 A1 | 3/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |

(56) References Cited

U.S. PATENT DOCUMENTS

| | | | |
|---|---|---|---|
| 2013/0116578 A1* | 5/2013 | An | A61B 5/7275 600/484 |
| 2013/0128690 A1 | 5/2013 | Gopalan | |
| 2013/0162433 A1 | 6/2013 | Muhsin et al. | |
| 2013/0190581 A1 | 7/2013 | Al-Ali et al. | |
| 2013/0190595 A1 | 7/2013 | Oraevsky | |
| 2013/0197328 A1 | 8/2013 | Diab et al. | |
| 2013/0243021 A1 | 9/2013 | Siskavich | |
| 2013/0253334 A1 | 9/2013 | Al-Ali et al. | |
| 2013/0274571 A1 | 10/2013 | Diab et al. | |
| 2013/0296672 A1 | 11/2013 | Dalvi et al. | |
| 2013/0317370 A1 | 11/2013 | Dalvi et al. | |
| 2013/0324808 A1 | 12/2013 | Al-Ali et al. | |
| 2013/0331670 A1 | 12/2013 | Kiani | |
| 2013/0338461 A1 | 12/2013 | Lamego et al. | |
| 2014/0012100 A1 | 1/2014 | Lamego et al. | |
| 2014/0025306 A1 | 1/2014 | Weber et al. | |
| 2014/0034353 A1 | 2/2014 | Al-Ali et al. | |
| 2014/0051953 A1 | 2/2014 | Lamego et al. | |
| 2014/0058230 A1 | 2/2014 | Abdul-Hafiz et al. | |
| 2014/0066783 A1 | 3/2014 | Kiani et al. | |
| 2014/0077956 A1 | 3/2014 | Sampath et al. | |
| 2014/0081100 A1 | 3/2014 | Muhsin et al. | |
| 2014/0081175 A1 | 3/2014 | Telfort | |
| 2014/0094667 A1 | 4/2014 | Schurman et al. | |
| 2014/0100434 A1 | 4/2014 | Diab et al. | |
| 2014/0114199 A1 | 4/2014 | Lamego et al. | |
| 2014/0120564 A1 | 5/2014 | Workman et al. | |
| 2014/0121482 A1 | 5/2014 | Merritt et al. | |
| 2014/0121483 A1 | 5/2014 | Kiani | |
| 2014/0127137 A1 | 5/2014 | Bellott et al. | |
| 2014/0128696 A1 | 5/2014 | Al-Ali | |
| 2014/0128699 A1 | 5/2014 | Al-Ali et al. | |
| 2014/0129702 A1 | 5/2014 | Lamego et al. | |
| 2014/0135588 A1 | 5/2014 | Al-Ali et al. | |
| 2014/0142401 A1 | 5/2014 | Al-Ali et al. | |
| 2014/0142402 A1 | 5/2014 | Al-Ali et al. | |
| 2014/0163344 A1 | 6/2014 | Al-Ali | |
| 2014/0163402 A1 | 6/2014 | Lamego et al. | |
| 2014/0166076 A1 | 6/2014 | Kiani et al. | |
| 2014/0171763 A1 | 6/2014 | Diab | |
| 2014/0180038 A1 | 6/2014 | Kiani et al. | |
| 2014/0180154 A1 | 6/2014 | Sierra et al. | |
| 2014/0194709 A1 | 7/2014 | Al-Ali et al. | |
| 2014/0194711 A1 | 7/2014 | Al-Ali | |
| 2014/0194766 A1 | 7/2014 | Al-Ali et al. | |
| 2014/0206963 A1 | 7/2014 | Diab et al. | |
| 2014/0213864 A1 | 7/2014 | Abdul-Hafiz et al. | |
| 2014/0243627 A1 | 8/2014 | Diab et al. | |
| 2014/0266790 A1 | 9/2014 | Al-Ali et al. | |
| 2014/0275808 A1 | 9/2014 | Poeze et al. | |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0275881 A1 | 9/2014 | Lamego et al. | |
| 2014/0288400 A1 | 9/2014 | Diab et al. | |
| 2014/0296664 A1 | 10/2014 | Bruinsma et al. | |
| 2014/0303520 A1 | 10/2014 | Telfort et al. | |
| 2014/0309506 A1 | 10/2014 | Lamego et al. | |
| 2014/0316228 A1 | 10/2014 | Blank et al. | |
| 2014/0323825 A1 | 10/2014 | Al-Ali et al. | |
| 2014/0330092 A1 | 11/2014 | Al-Ali et al. | |
| 2014/0330098 A1 | 11/2014 | Merritt et al. | |
| 2014/0330099 A1 | 11/2014 | Al-Ali et al. | |
| 2014/0333440 A1 | 11/2014 | Kiani | |
| 2014/0336481 A1 | 11/2014 | Shakespeare et al. | |
| 2014/0343436 A1 | 11/2014 | Kiani | |
| 2015/0018650 A1 | 1/2015 | Al-Ali et al. | |
| 2016/0051205 A1* | 2/2016 | Al-Ali | G16H 40/63 600/301 |

FOREIGN PATENT DOCUMENTS

| | | |
|---|---|---|
| EP | 0659058 | 1/1999 |
| EP | 1207536 | 5/2002 |
| GB | 2358546 | 11/1999 |
| JP | 6214898 | 1/1987 |
| JP | 01-309872 | 6/1998 |
| JP | 10-155755 | 6/1998 |
| JP | 2001-50713 | 5/1999 |
| JP | 2003-329719 | 11/2003 |
| WO | WO 1994/005207 | 3/1994 |
| WO | WO 1994/013207 | 6/1994 |
| WO | WO 1995/029632 | 11/1995 |
| WO | WO 1999/053277 | 10/1999 |
| WO | WO 2000/010462 | 3/2000 |
| WO | WO 2001/034033 | 5/2001 |
| WO | WO 2001/078059 | 10/2001 |
| WO | WO 2001/097691 | 12/2001 |
| WO | WO 2002/003042 | 1/2002 |
| WO | WO 2003/058646 | 7/2003 |
| WO | WO 2003/087737 | 10/2003 |
| WO | WO 2004/000111 | 12/2003 |
| WO | WO 2004/004411 | 1/2004 |
| WO | WO 2005/096931 | 10/2005 |
| WO | WO 2005/099562 | 10/2005 |
| WO | WO 2008/017246 | 2/2008 |
| WO | WO 2008/080469 | 7/2008 |
| WO | WO 2008/148172 | 12/2008 |
| WO | WO 2009/093159 | 7/2009 |
| WO | WO 2009/137524 | 11/2009 |

OTHER PUBLICATIONS

US 9,579,050 B2, 02/2017, Al-Ali (withdrawn)
GE Healthcare, "Transport ProTM Patient Monitor Operator's Manual" Apr. 9, 2007, in 286 pages.
Analog Devices, 12-Bit Serial Input Multiplying D/A Converter, Product Data Sheet, 2000.
Chambrin, M-C.; "Alarms in the intensive care unit: how can the number of false alarms be reduced?"; Critical Care Aug. 2001, vol. 5 No. 4; p. 1-5.
Eldor et al., "A device for monitoring ventilation during anaesthesia; the paratracheal audible respiratory monitor", Canadian Journal of Anaesthesia, 1990, vol. 9, No. 1, p. 95-98.
Gorges, M. et al; "Improving Alarm Performance in the Medical Intensive Care Unit Using Delays and Clinical Context"; Technology, Computing, and Simulation; vol. 108, No. 5, May 2009; p. 1546-1552.
Imhoff, M. et al; "Alarm Algorithms in Critical Care Monitoring"; Anesth Analg 2006;102:1525-37.
International Search Report & Written Opinion, PCT Application PCT/US2010/052758, dated Feb. 10, 2011; 12 pages.
International Search Report & Written Opinion, PCT Application PCT/US2010/058981, dated Feb. 17, 2011; 11 pages.
International Search Report and Written Opinion issued in application No. PCT/US2010/052756 dated Feb. 6, 2012.
International Search Report, PCT Application PCT/CA2003/000536, dated Dec. 11, 2003; 2 pages.
International Search Report, PCT Application PCT/US2009/069287, dated Mar. 30, 2010; 7 pages.
Japanese Office Action for JP Application No. 2007-506626 dated Mar. 1, 2011.
Sierra et al., Monitoring Respiratory Rate Based on Tracheal Sounds. First Experieances, Proceedings of the 26th Annual Int'l Conf. of the IEEE EMBS (Sep. 2004), 317-320.
Watt, R. C.; "Alarms and Anesthesia. Challenges in the design of Intelligent systems for Patient Monitoring"; IEEE Engineering in Medicine and biology; Dec. 1993, p. 34-41.
Welch Allyn, ECG ASIC, Product Data Sheete, 2001.
Supplementary Partial European Search Report for International Application No. 05732095.4, dated Jun. 26, 2009 in 4 pages.
Theimer et al., "Definitions of audio features for music content description", Algorithm Engineering Report TR08-2-001, Feb. 2008.

(56) References Cited

OTHER PUBLICATIONS

Stewart, C., Larson, V., "Detection and classification of acoustic signals from fixed-wing aircraft," Systems Engineering, CH3051-0/91/0000-0025, IEEE, 1991.
Johnston, Development of a Signal Processing Library for Extraction of Sp02, HR, HRV, and RR from Photoplethysmographic Waveforms, Thesis: Degree of Master of Science, Worcester Polytechnic Institute, date of presentation/defense Jul. 17, 2006, date listed Jul. 27, 2006.
U.S. Appl. No. 15/669,201, Respirator Processor, filed Aug. 4, 2017.
U.S. Appl. No. 14/206,900, Acoustic Pulse and Respiration Monitoring System, filed Mar. 12, 2014.
U.S. Appl. No. 14/636,500, Acoustic Pulse and Respiration Monitoring System, filed Mar. 3, 2015.
U.S. Appl. No. 14/207,248, Acoustic Respiratory Event Processor, filed Mar. 12, 2014.
U.S. Appl. No. 15/095,912, Plethysmographic Respiration Rate Detection, filed Apr. 11, 2016.
U.S. Appl. No. 13/651,283, Respiration Event Processor, filed Oct. 12, 2012.

\* cited by examiner

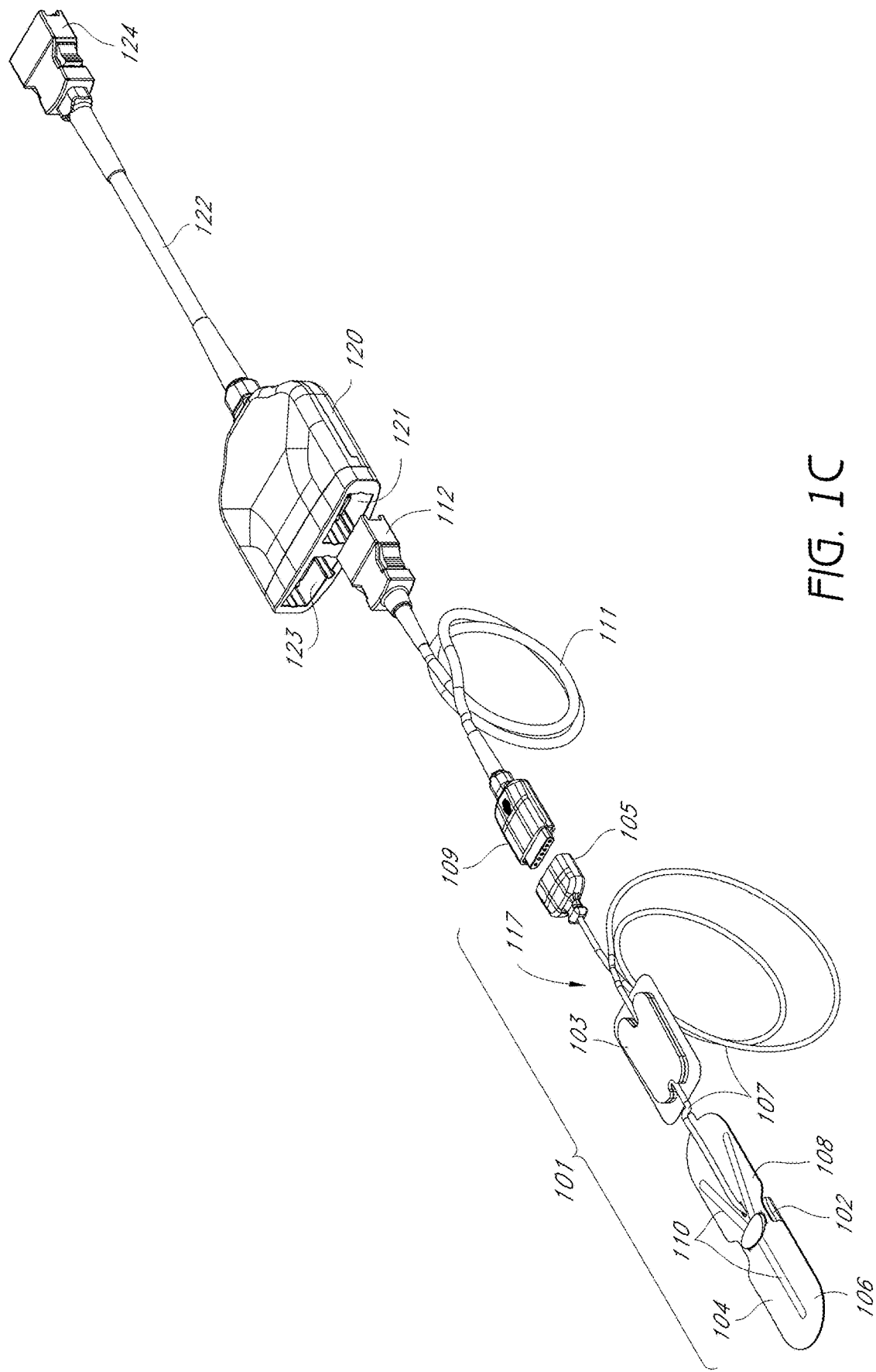

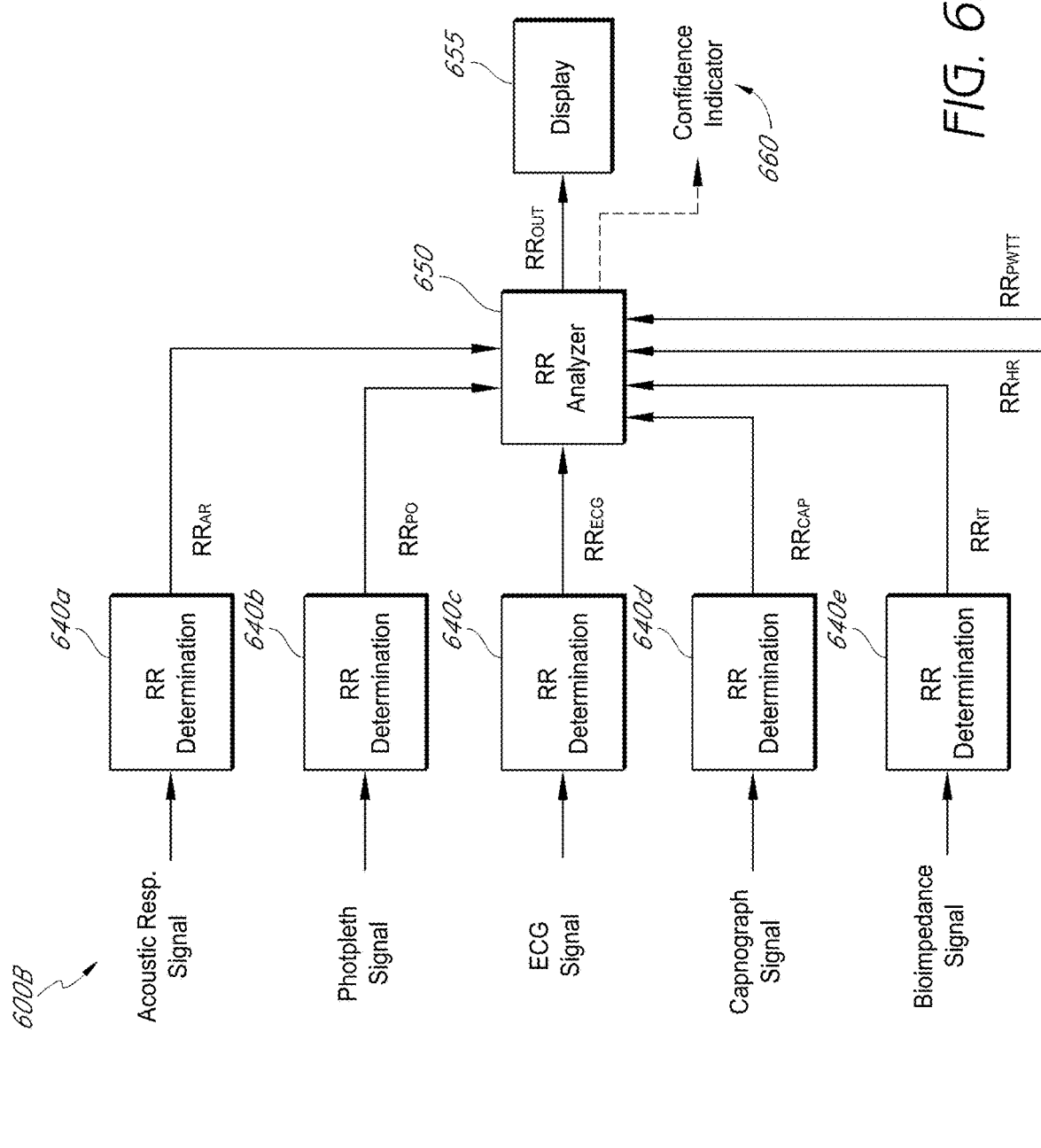

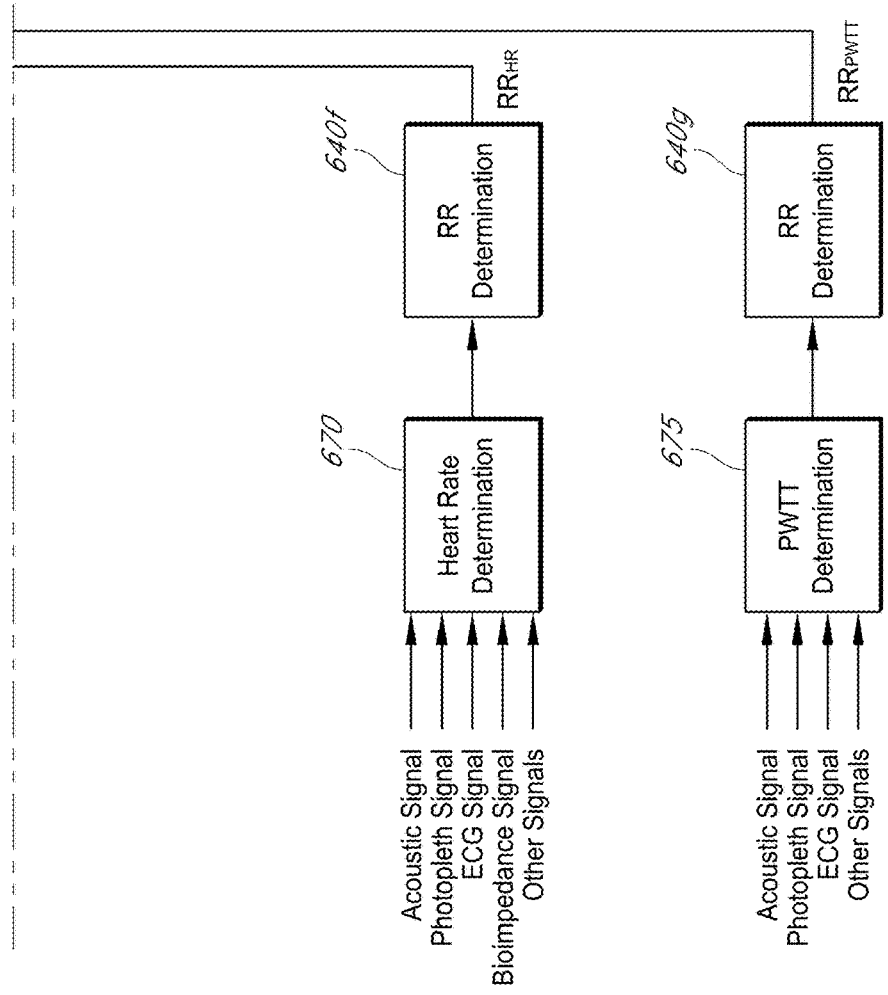

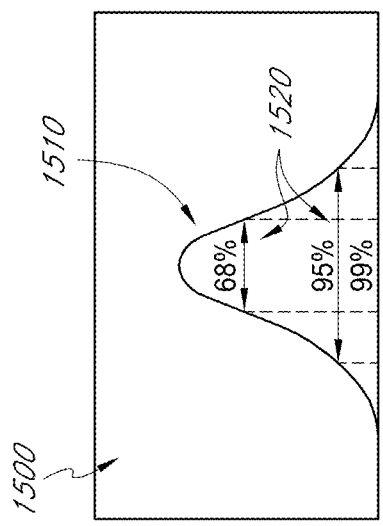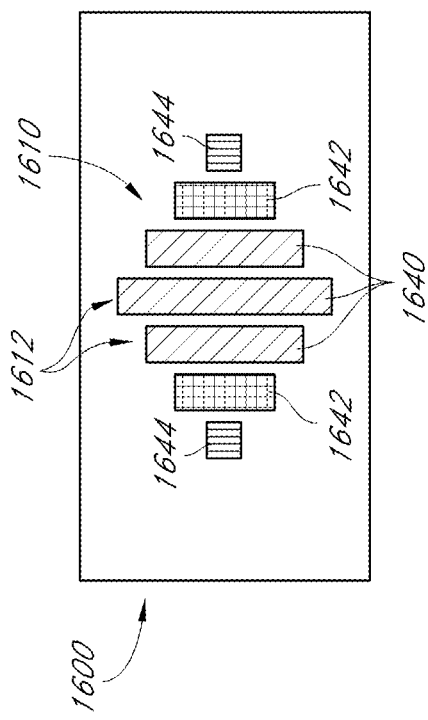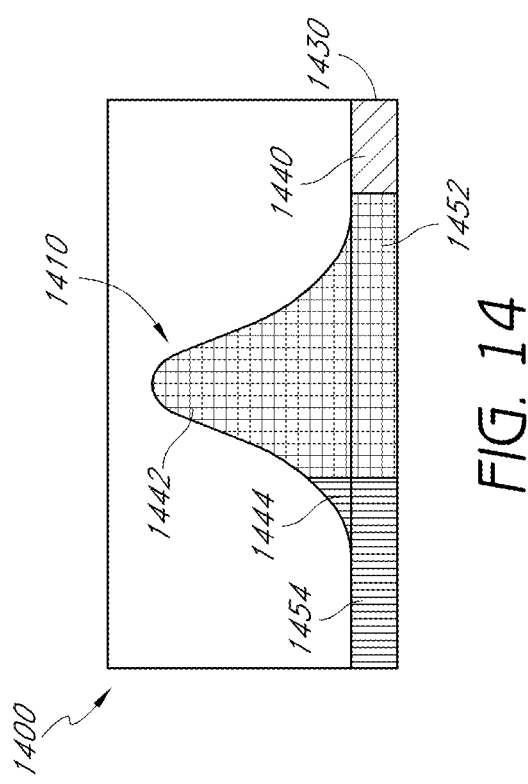

SYSTEM AND METHOD FOR MONITORING RESPIRATORY RATE MEASUREMENTS

RELATED APPLICATIONS

This application is a continuation of U.S. patent application Ser. No. 14/752,466, filed Jun. 26, 2015, entitled "SYSTEM FOR DETERMINING CONFIDENCE IN RESPIRATORY RATE MEASUREMENTS," which is a continuation of U.S. patent application Ser. No. 12/905,449, filed Oct. 15, 2010, entitled "SYSTEM FOR DETERMINING CONFIDENCE IN RESPIRATORY RATE MEASUREMENTS," which claims priority from U.S. Provisional Patent Application No. 61/252,086 filed Oct. 15, 2009, entitled "Pulse Oximetry System for Determining Confidence in Respiratory Rate Measurements," from U.S. Provisional Patent Application No. 61/261,199, filed Nov. 13, 2009, entitled "Pulse Oximetry System with Adjustable Alarm Delay," and from U.S. Provisional Patent Application No. 61/366,866, filed Jul. 22, 2010, entitled "Pulse Oximetry System for Determining Confidence in Respiratory Rate Measurements," the disclosures of which are hereby incorporated by reference in their entirety.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a patient's physiological parameters. Physiological parameters include, for example, blood pressure, respiratory rate, oxygen saturation ($SpO_2$) level, other blood constitutions and combinations of constituents, and pulse, among others. Clinicians, including doctors, nurses, and certain other caregiver personnel use the physiological parameters obtained from the patient to diagnose illnesses and to prescribe treatments. Clinicians can also use the physiological parameters to monitor a patient during various clinical situations to determine whether to increase the level of care given to the patient. Various patient monitoring devices are commercially available from Masimo Corporation ("Masimo") of Irvine, Calif.

During and after surgery and in other care situations, respiratory rate is a frequently monitored physiological parameter of a patient. Respiratory rate can be indicated as the number of breaths a person takes within a certain amount of time, such as breaths per minute. For example, a clinician (such as a nurse, doctor, or the like) can use respiratory rate measurements to determine whether a patient is experiencing respiratory distress and/or dysfunction.

SUMMARY OF DISCLOSURE

A system for determining multiparameter confidence in a respiratory rate measurement from a medical patient, the system comprising: an optical sensor comprising: a light emitter configured to impinge light on body tissue of a living patient, the body tissue comprising pulsating blood, and a detector responsive to the light after attenuation by the body tissue, wherein the detector is configured to generate a photoplethysmographic signal indicative of a physiological characteristic of the living patient; an ECG sensor configured to obtain an electrical signal from the living patient; an acoustic sensor, the acoustic sensor configured to obtain an acoustic respiratory signal from the living patient; and a processor configured to: derive a first respiratory rate measurement from the acoustic respiratory signal, derive a second respiratory rate measurement from one or both of the photoplethysmographic signal and the electrical signal, and use the second respiratory rate measurement to calculate a confidence in the first respiratory rate measurement.

A system for determining confidence in a respiratory rate measurement from a medical patient, the system comprising: a first physiological sensor configured to obtain a physiological signal from a patient, the first physiological sensor comprising at least one of the following: an ECG sensor, a bioimpedance sensor, and a capnography sensor; an acoustic sensor configured to obtain an acoustic respiratory signal from the living patient; and a processor configured to: obtain a first respiratory rate measurement from the physiological signal, obtain a second respiratory rate measurement from the acoustic respiratory signal, and calculate a confidence in the first respiratory rate measurement responsive to the first and second respiratory rate measurements.

A method of analyzing respiratory rate monitoring parameters to determine confidence in a measured respiratory rate, the method comprising: obtaining a first respiratory measurement from a first physiological device, the first physiological device comprising an acoustic sensor; obtaining a second respiratory measurement from a second physiological device; determining a third respiratory rate measurement based at least in part on the first and second respiratory rate measurements; and outputting the third respiratory rate measurement.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIG. 1C is a top perspective view illustrating portions of a sensor assembly in accordance with an embodiment of the disclosure;

FIGS. 6A through 6C illustrate block diagrams of embodiments of respiratory rate measurement calculation systems.

FIGS. 11 through 17 illustrate embodiments of parameter confidence displays.

DETAILED DESCRIPTION

Figure 1A:
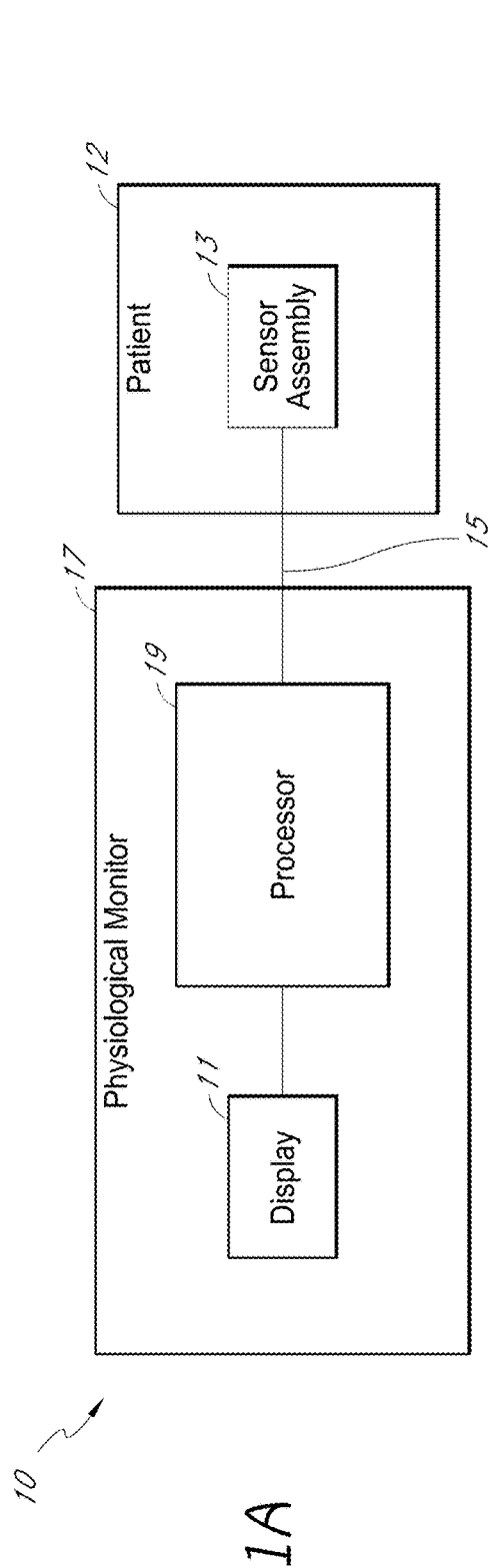
FIGS. 1A-B are block diagrams illustrating physiological monitoring systems in accordance with embodiments of the disclosure.

Acoustic sensors, including piezoelectric acoustic sensors, can be used to measure breath sounds and other biological sounds of a patient. Breath sounds obtained from an acoustic sensor placed on the neck, chest, and/or other suitable location can be processed by a patient monitor to derive one or more physiological parameters of a patient, including respiratory rate. Respiratory rate can also be determined from other physiological signals (for example, an ECG signal, a plethysmographic signal, a bioimpedance signal, and/or the like) obtained using other sensors and/or instruments.

Respiratory rate measurements derived from a single sensor or sensor type can be less accurate at times due to noise, sensor limitations, body movement, and/or other reasons. Accordingly, improved multiparameter respiratory rate measurements can be obtained by jointly processing multiple physiological signals from multiple sensors and/or sensor types. Alternately, or in addition, respiratory rate measurements derived from a physiological signal obtained from one type of sensor can be used to continuously or periodically refine or assess confidence in the respiratory rate measurements derived from a physiological signal obtained from another type of sensor. For example, in certain embodiments, respiratory rate measurements derived from a plethysmographic signal obtained by an optical sensor can be used to improve or determine confidence in the respiratory rate derived from an acoustic signal obtained by an acoustic sensor.

This disclosure describes, among other features, systems and methods for using multiple physiological signals to improve respiratory or other physiological parameter measurements reflective of a patient's condition and/or to determine confidence in these physiological parameter measurements. In certain embodiments, a patient monitoring system comprises one or more physiological sensors applied to a living patient and a processor to monitor the physiological signals received from physiological sensors. The physiological sensors can include, for example, acoustic sensors for acquiring breath and/or heart sounds, electrodes for acquiring ECG and/or bioimpedance signals, and noninvasive optical sensors to perform pulse oximetry and related noninvasive analysis of blood constituents.

In particular, in certain embodiments, a patient monitoring system can programmatically determine multiparameter confidence in respiratory rate measurements obtained from an acoustic sensor based at least partly on inputs obtained from other non-acoustic sensors or monitors. The patient monitoring system can output a multiparameter confidence indication reflective of the programmatically-determined multiparameter confidence. The multiparameter confidence indication can assist a clinician in determining whether or how to treat a patient based on the patient's respiratory rate.

In certain embodiments, the patient monitoring system can determine the multiparameter confidence at least in part by receiving signals from multiple physiological parameter monitoring devices that are reflective of respiratory rate. For example, a multiparameter patient monitoring unit can receive a signal reflective of a respiratory rate from both an acoustic sensor and an optical sensor. Respiratory rate measurements can be extracted and/or derived from each of the physiological parameter signals. The respiratory rate measurement from the acoustic sensor can be compared with the respiratory rate measurement derived from the optical sensor signal. Based at least partly on this comparison, a determination of multiparameter confidence in the acoustically-derived respiratory rate can be made. A visual or audible indicator corresponding to this multiparameter confidence determination, including possibly an alarm, can be output for presentation to a clinician.

Additionally, in certain embodiments, the respiratory rate measurement output to the clinician can be generated based at least partly on a combination of the multiple respiratory rate measurements. For example, a respiratory rate measurement derived from an optical sensor signal can be combined with a respiratory rate measurement derived from an acoustic sensor signal to produce an overall respiratory rate. The overall respiratory rate measurement can be output to the patient monitor display and/or can be output over a network to another device.

Moreover, in certain embodiments, the patient monitoring systems and methods disclosed herein can assess multiparameter confidence and/or determine respiratory rate based at least partly on signals received from other physiological parameter monitoring devices. For example, various measurements obtained from a capnograph, an electrocardiograph (ECG), a bioimpedance device, or from other monitoring devices or sensors can be used to assess multiparameter confidence in acoustic respiratory rate measurements and/or to determine an overall respiratory rate output.

For purposes of illustration, this disclosure is described primarily in the context of respiratory rate. However, the features described herein can be applied to other respiratory parameters, including, for example, inspiratory time, expiratory time, inspiratory to expiratory ratio, inspiratory flow, expiratory flow, tidal volume, minute volume, apnea duration, breath sounds (including, e.g., rales, rhonchi, or stridor), changes in breath sounds, and the like. Moreover, the features described herein can also be applied to other physiological parameters and/or vital signs. For example, outputs from multiple monitoring devices or sensors (e.g., an optical sensor and an ECG monitor) can be used to assess multiparameter confidence in heart rate measurements, among other parameters.

Figure 1B:
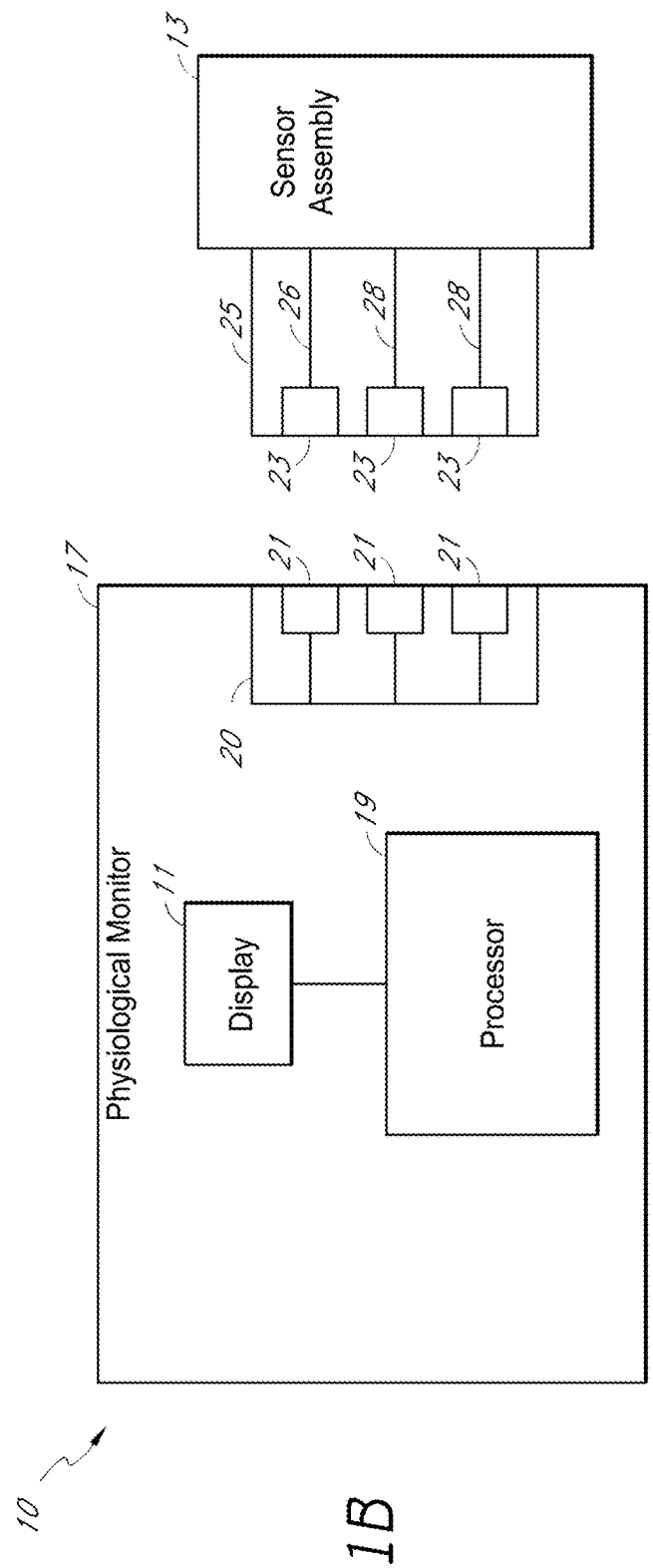

Referring to the drawings, FIGS. 1A through 1C illustrate example patient monitoring systems, sensors, and cables that can be used to derive a respiratory rate measurement from a patient. FIGS. 2 through 8 illustrate multiparameter respiratory rate embodiments. The embodiments of FIGS. 2 through 8 can be implemented at least in part using the systems and sensors described in FIGS. 1A through 1C.

Turning to FIG. 1A, an embodiment of a physiological monitoring system 10 is shown. In the physiological monitoring system 10, a medical patient 12 is monitored using one or more sensor assemblies 13, each of which transmits a signal over a cable 15 or other communication link or medium to a physiological monitor 17. The physiological monitor 17 includes a processor 19 and, optionally, a display 11. The one or more sensors 13 include sensing elements such as, for example, acoustic piezoelectric devices, electrical ECG leads, optical sensors, or the like. The sensors 13 can generate respective signals by measuring a physiological parameter of the patient 12. The signals are then processed by one or more processors 19. The one or more processors 19 then communicate the processed signal to the display 11. In an embodiment, the display 11 is incorporated in the physiological monitor 17. In another embodiment, the display 11 is separate from the physiological monitor 17. In one embodiment, the monitoring system 10 is a portable monitoring system. In another embodiment, the monitoring system 10 is a pod, without a display, that is adapted to provide physiological parameter data to a display.

For clarity, a single block is used to illustrate the one or more sensors 13 shown in FIG. 1A. It should be understood that the sensor 13 shown is intended to represent one or more sensors. In an embodiment, the one or more sensors 13 include a single sensor of one of the types described below. In another embodiment, the one or more sensors 13 include one or more acoustic sensors. In still another embodiment, the one or more sensors 13 include one or more acoustic sensors and one or more ECG sensors, optical sensors, bioimpedance sensors, capnography sensors, and the like. In each of the foregoing embodiments, additional sensors of different types are also optionally included. Other combinations of numbers and types of sensors are also suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensors 13.

As shown in FIG. 1B, the acoustic sensor assembly 13 can include a cable 25. The cable 25 can include three conductors within an electrical shielding. One conductor 26 can provide power to a physiological sensor 13, one conductor 28 can provide a ground signal from the physiological monitor 17, and one conductor 28 can transmit signals from the sensor 13 to the physiological monitor 17. For multiple sensors 13, one or possibly more cables 13 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor assembly 13 and the physiological monitor 17 communicate wirelessly.

FIG. 1C illustrates an embodiment of a sensor system 100 including a sensor assembly 101 and a monitor cable 111 suitable for use with any of the physiological monitors shown in FIGS. 1A and 1B. The sensor assembly 101 includes a sensor 115, a cable assembly 117, and a connector 105. The sensor 115, in one embodiment, includes a sensor subassembly 102 and an attachment subassembly 104. The cable assembly 117 of one embodiment includes a sensor 107 and a patient anchor 103. A sensor connector subassembly 105 is connected to the sensor cable 107.

The sensor connector subassembly 105 can be removably attached to an instrument cable 111 via an instrument cable connector 109. The instrument cable 111 can be attached to a cable hub 120, which includes a port 121 for receiving a connector 112 of the instrument cable 111 and a second port 123 for receiving another cable. In certain embodiments, the second port 123 can receive a cable connected to an optical sensor or other sensor. In addition, the cable hub 120 could include additional ports in other embodiments for receiving additional cables. The hub includes a cable 122 which terminates in a connector 124 adapted to connect to a physiological monitor (not shown).

The sensor connector subassembly 105 and connector 109 can be configured to allow the sensor connector 105 to be straightforwardly and efficiently joined with and detached from the connector 109. Embodiments of connectors having connection mechanisms that can be used for the connectors 105, 109 are described in U.S. patent application Ser. No. 12/248,856 (hereinafter referred to as "the '856 application"), filed on Oct. 9, 2008, which is incorporated in its entirety by reference herein. For example, the sensor connector 105 could include a mating feature (not shown) which mates with a corresponding feature (not shown) on the connector 109. The mating feature can include a protrusion which engages in a snap fit with a recess on the connector 109. In certain embodiments, the sensor connector 105 can be detached via one hand operation, for example. Examples of connection mechanisms can be found specifically in paragraphs [0042], [0050], [0051], [0061]-[0068] and [0079], and with respect to FIGS. 8A-F, 13A-E, 19A-F, 23A-D and 24A-C of the '856 application, for example.

The sensor connector subassembly 105 and connector 109 can reduce the amount of unshielded area in and generally provide enhanced shielding of the electrical connection between the sensor and monitor in certain embodiments. Examples of such shielding mechanisms are disclosed in the '856 application in paragraphs [0043]-[0053], [0060] and with respect to FIGS. 9A-C, 11A-E, 13A-E, 14A-B, 15A-C, and 16A-E, for example.

In an embodiment, the acoustic sensor assembly 101 includes a sensing element, such as, for example, a piezoelectric device or other acoustic sensing device. The sensing element can generate a voltage that is responsive to vibrations generated by the patient, and the sensor can include circuitry to transmit the voltage generated by the sensing element to a processor for processing. In an embodiment, the acoustic sensor assembly 101 includes circuitry for detecting and transmitting information related to biological sounds to a physiological monitor. These biological sounds can include heart, breathing, and/or digestive system sounds, in addition to many other physiological phenomena. The acoustic sensor 115 in certain embodiments is a biological sound sensor, such as the sensors described herein. In some embodiments, the biological sound sensor is one of the sensors such as those described in the '883 application. In other embodiments, the acoustic sensor 115 is a biological sound sensor such as those described in U.S. Pat. No. 6,661,161, which is incorporated by reference herein in its entirety. Other embodiments include other suitable acoustic sensors.

The attachment sub-assembly 104 includes first and second elongate portions 106, 108. The first and second elongate portions 106, 108 can include patient adhesive (e.g., in some embodiments, tape, glue, a suction device, etc.). The adhesive on the elongate portions 106, 108 can be used to secure the sensor subassembly 102 to a patient's skin. One or more elongate members 110 included in the first and/or second elongate portions 106, 108 can beneficially bias the sensor subassembly 102 in tension against the patient's skin and reduce stress on the connection between the patient adhesive and the skin. A removable backing can be provided with the patient adhesive to protect the adhesive surface prior to affixing to a patient's skin.

The sensor cable 107 can be electrically coupled to the sensor subassembly 102 via a printed circuit board ("PCB") (not shown) in the sensor subassembly 102. Through this contact, electrical signals are communicated from the multiparameter sensor subassembly to the physiological monitor through the sensor cable 107 and the cable 111.

In various embodiments, not all of the components illustrated in FIG. 1C are included in the sensor system 100. For example, in various embodiments, one or more of the patient anchor 103 and the attachment subassembly 104 are not included. In one embodiment, for example, a bandage or tape is used instead of the attachment subassembly 104 to attach the sensor subassembly 102 to the measurement site. Moreover, such bandages or tapes can be a variety of different shapes including generally elongate, circular and oval, for example. In addition, the cable hub 120 need not be included in certain embodiments. For example, multiple cables from different sensors could connect to a monitor directly without using the cable hub 120.

Additional information relating to acoustic sensors compatible with embodiments described herein, including other embodiments of interfaces with the physiological monitor, are included in U.S. patent application Ser. No. 12/044,883, filed Mar. 7, 2008, entitled "Systems and Methods for Determining a Physiological Condition Using an Acoustic Monitor," (hereinafter referred to as "the '883 application"), the disclosure of which is hereby incorporated by reference in its entirety. An example of an acoustic sensor that can be used with the embodiments described herein is disclosed in U.S. Patent Application No. 61/252,076, filed Oct. 15, 2009, titled "Acoustic Sensor Assembly," the disclosure of which is hereby incorporated by reference in its entirety.

Figure 2:
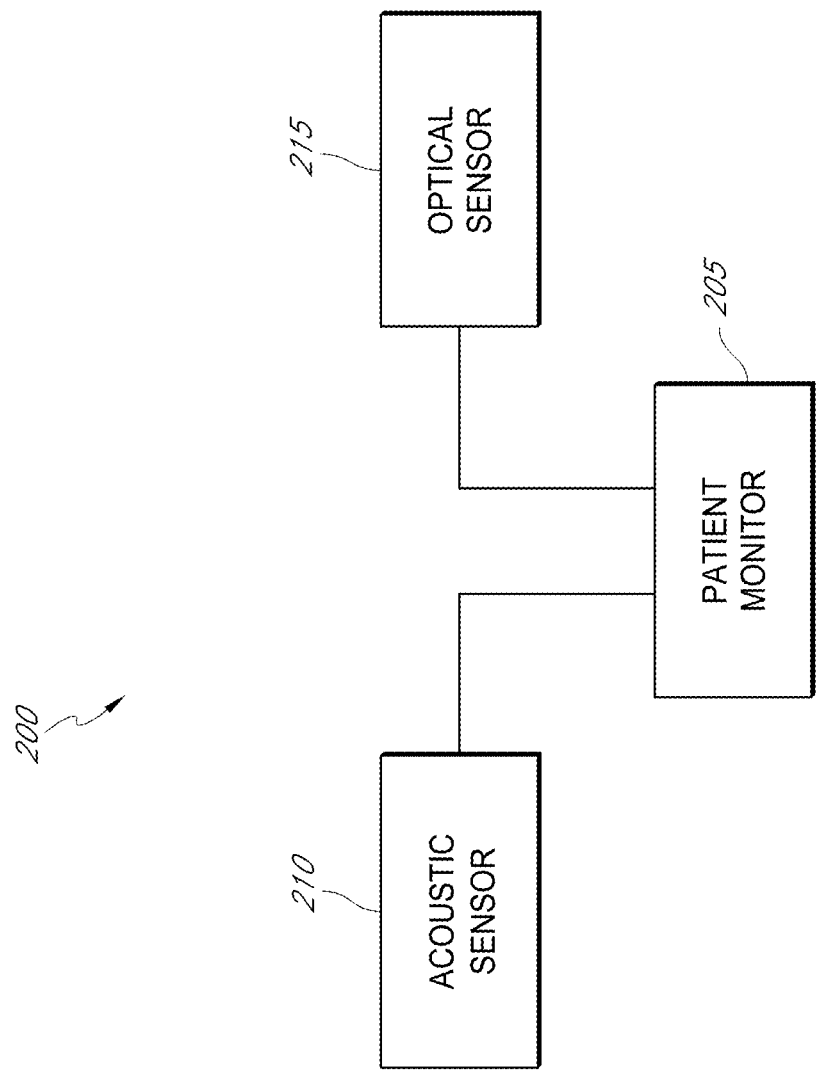
FIG. 2 illustrates a block diagram of an embodiment of a multiparameter patient monitoring system that includes an acoustic respiratory monitoring (ARM) sensor and an optical sensor.

FIG. 2 illustrates an embodiment of a multiparameter patient monitoring system 200, which can implement any of the features described above. The multiparameter patient monitoring system 200 includes a multiparameter patient monitor 205 that receives signals from multiple physiological parameter measurement devices. The multiparameter patient monitor 205 can use the multiple received signals to determine a confidence value for respiratory rate measurements derived from the signals. The confidence value can advantageously reflect a degree to which the respiratory rate measurements derived from the different signals correspond. In addition, in some embodiments, the multiparameter patient monitor 205 can generate one or more respiratory rate outputs based at least partly on the multiple received signals.

The patient monitor 205 can include any of the features of the physiological monitor 17 described above. The patient monitor 205 can include one or more processors, a display, memory, one or more input/output (I/O) devices (such as input control buttons, speakers, etc), a wireless transceiver, a power supply, and/or processing and filtration circuitry. In certain embodiments, the patient monitor 205 can communicate with external devices, such as processing devices, output devices, mass storage devices, and the like. The patient monitor 205 can communicate with the external devices via a wired and/or wireless connection. The external devices can include a central monitoring station (such as a nurses' monitoring station), a server, a laptop computer, a cell phone, a smart phone, a personal digital assistant, a kiosk, other patient monitors, or other clinician devices. The patient monitor 205 can send physiological data to the external devices.

In the depicted embodiment, the patient monitor 205 is in communication with an acoustic sensor 210 and an optical sensor 210. The acoustic sensor 210 can be a piezoelectric sensor or the like that obtains physiological information reflective of one or more respiratory parameters of a patient, including respiratory rate, expiratory flow, tidal volume, minute volume, apnea duration, breath sounds, riles, rhonchi, stridor, and changes in breath sounds, such as decreased volume or change in airflow. In addition, in some cases the acoustic sensor 210 can measure other physiological sounds, such as heart rate (e.g., to help with probe-off detection). In certain embodiments, the acoustic sensor 210 can include any of the features described in U.S. Patent Application No. 61/252,076, filed Oct. 15, 2009, titled "Acoustic Sensor Assembly," the disclosure of which is hereby incorporated by reference in its entirety.

The optical sensor 215 can include a noninvasive optical sensor that obtains physiological information reflective of one or more blood parameters of the patient. These parameters can include one or more of the following: a photoplethysmograph, oxygen saturation ($SpO_2$), HbCO, HBMet, $FaO_2$, fractional oxygen, total hemoglobin (Hbt), other hemoglobin species, carbon monoxide, carbon dioxide, pulse rate, perfusion index, pleth variability index, and optionally others, including concentrations or actual analyte values of the same. The optical sensor 215 can include one or more emitters capable of irradiating a tissue site (such as a finger) with one or more wavelengths of light, such as red and/or infrared (IR) wavelengths. In one embodiment, the optical sensor 215 is a pulse oximetry sensor. While many optical sensors emit two wavelengths, certain of the features described herein can be implemented by a photoplethysmograph sensor that emits a single wavelength. Further, the optical sensor 215 need not emit red or infrared wavelengths in certain embodiments but can also emit other wavelengths. The optical sensor 215 can also include one or more detectors capable of detecting the light after attenuation by pulsatile blood and tissue at the measurement site. The one or more detectors can generate a signal responsive to the attenuated light, which can be provided to the patient monitor 205.

The patient monitor 205 can receive signals indicative of one or more physiological parameters from the acoustic sensor 210 and from the optical sensor 215. The patient monitor 205 can extract and/or derive respiratory rate measurements from signals provided by both the acoustic sensor 210 and the optical sensor 215. The patient monitor 205 can also output one or more respiratory rate measurements for display based at least in part on the received signals. Example techniques for deriving respiratory rate from the optical sensor measurements are described below with respect to FIG. 3.

In certain embodiments, the patient monitor 205 can use pulse oximetry respiratory rate measurements to determine a multiparameter confidence in the acoustic respiratory rate measurements. The multiparameter confidence can be a value that reflects a degree of correspondence between the respiratory rate measurements obtained from the two sensors 210, 215. A close correspondence (e.g., small difference) between the two respiratory rate measurements can cause the patient monitor 205 to assign a higher multiparameter confidence to the acoustic respiratory rate measurement. Conversely, a larger difference between the two measurements can result in a lower multiparameter confidence. In certain embodiments, the patient monitor 205 can instead or also use the difference in respiratory rate values to assign a multiparameter confidence to the pulse-oximetry-derived respiratory rate measurement.

More generally, any comparative metric can be used to determine the multiparameter confidence. The comparative metric can be a difference between the measurements of the two sensors 210, 215 but need not be. Instead, in some embodiments, the comparative metric can be a ratio between the measurements from the sensors 210, 215, a percentage derived from such a ratio, or the like. Such a ratio or percentage might be more meaningful than an absolute difference in some situations. Similarly, the comparative metric can be a normalization of the measurements from the two sensors 210, 215, such as the following quotient: (the acoustic respiratory rate—the oximeter respiratory rate)/(the acoustic respiratory rate) or the like. Other comparative metrics can also be used.

Additionally, the patient monitor 205 can use pulse oximetry respiratory rate measurements to refine or adjust the acoustic respiratory rate measurements in some implementations. For example, the respiratory rate measurements derived from the two sensors 210, 215 can be combined to form an overall respiratory measurement. The patient monitor 205 can average the two measurements, for example. The combined respiratory rate measurement can be more accurate than a respiratory rate measurement from either sensor 210, 215 alone.

The patient monitor 205 can output the respiratory rate measurement derived from either or both of the acoustic and optical sensors 210, 215. In addition, the patient monitor 205 can output a multiparameter confidence indicator that reflects the calculated multiparameter confidence. Examples of multiparameter confidence indicators are described in greater detail below.

Figure 3A:
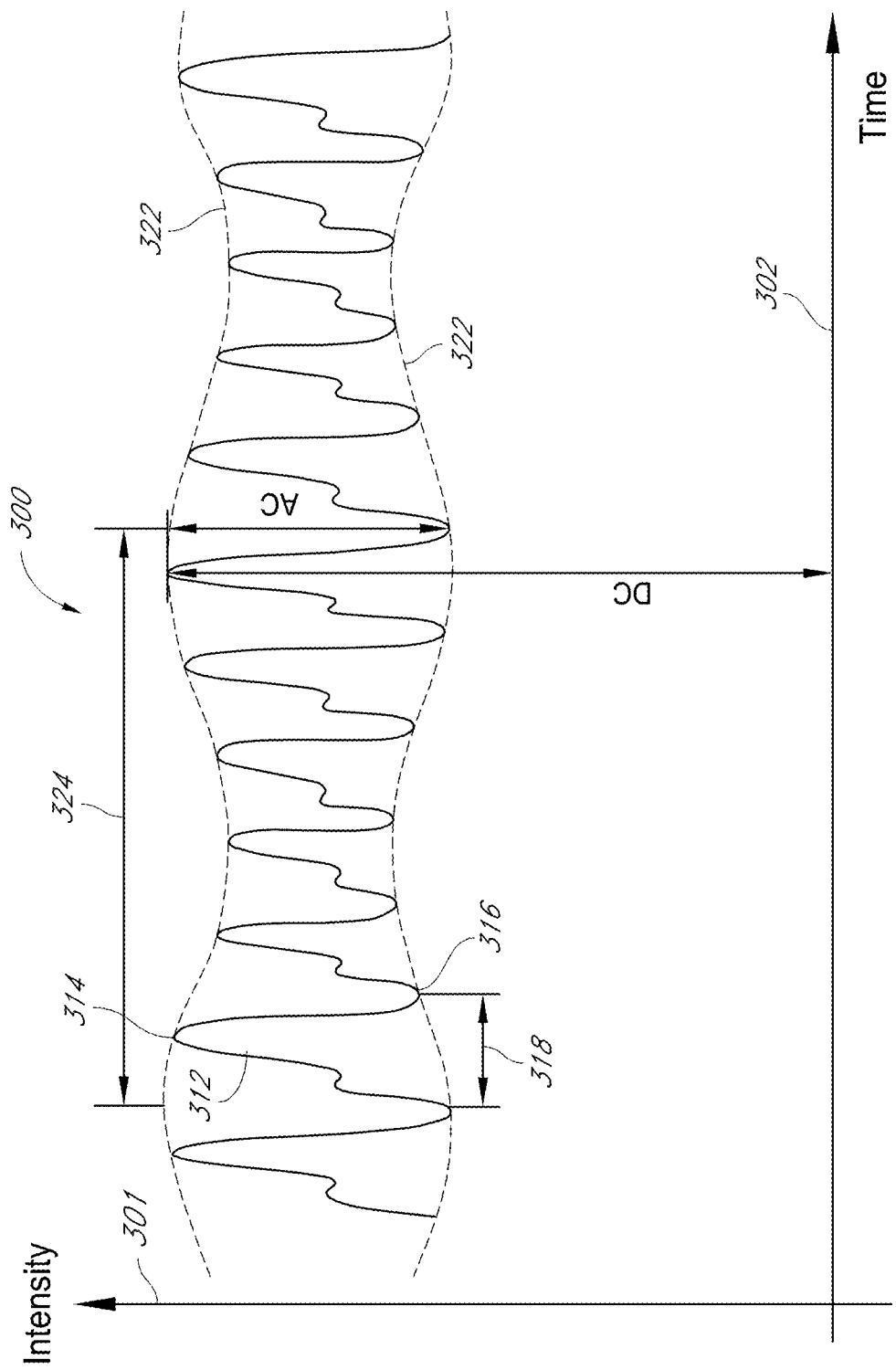
FIG. 3A illustrates an embodiment of an envelope of a photoplethysmograph waveform.

In certain embodiments, a signal received from the optical sensor 215 can be analyzed to determine a respiratory rate measurement. As an illustration of such a signal, FIG. 3A depicts an example photoplethysmograph (pleth) waveform 300 derived from an optical sensor. The pleth waveform 300 can be derived from the received signal by the patient monitor 205. The pleth waveform 300 is plotted on an intensity axis 301 versus a time axis 302. The pleth waveform 300 has multiple pulses 312, each with a peak 314 and a valley 316 and extending over a time period 318. A curve extending along the peaks 314 of the pleth waveform 300 represents an envelope 322 of the pleth waveform 300.

In certain embodiments, a respiratory rate measurement can be determined from an analysis of the pleth waveform 300. A respiratory rate measurement can be determined from the pleth waveform 300 in the time domain and/or in the frequency domain. In certain embodiments, a respiratory rate measurement can be determined from the modulation in the amplitude of the pleth waveform 300. For example, the time-varying frequency of the envelope 322 can correspond to the respiratory rate of the patient. The frequency of the pleth envelope 322 can be determined from the inverse of the period 324 of the envelope 322. The envelope 322 of the pleth waveform 300 can be detected by an envelope detector. The envelope can be identified using an analog envelope detector such as a diode-based envelope detector or a digital detector employing such techniques as a Hilbert transform, squaring and low-pass filtering, or the like.

The respiratory rate can also be determined from a frequency analysis of the pleth waveform 300. A frequency spectrum of the pleth waveform 300 can be generated, for example, by performing a Fast Fourier Transform (FFT) or other mathematical transform of the pleth waveform 300. The respiratory rate can be identified by a peak in the spectrum (e.g., which corresponds to the frequency of the pleth envelope 322). In certain embodiments, the peak can be identified by identifying the highest peak in a range of typical respiratory rates of a human patient. This range can differ for different patients based on factors such as age, gender, comorbidity, and the like. A respiratory rate value can be derived from the frequency of the selected peak. Additional methods of determining respiratory rate from the pleth waveform 300 and/or an optical signal are also possible.

In certain embodiments, instead of or in addition to analyzing the pleth waveform 300 to obtain respiratory rate, the patient monitor 205 can obtain respiratory rate from variability detected in oxygen saturation measurements obtained from the optical sensor 215. Variations in the oxygen saturation can track or approximately track the patient's respiratory cycle (e.g., a cycle of recruitment and collapse of alveoli), as is described in greater detail in U.S. Application No. 61/222,087, filed Jun. 30, 2009, titled "Pulse Oximetry System for Adjusting Medical Ventilation," the disclosure of which is hereby incorporated by reference in its entirety. The magnitude of the time-domain variations in the oxygen saturation can reflect the degree of recruitment and collapse of alveoli in the respiratory cycle. In the frequency domain, a peak in a magnitude response of the $SpO_2$ variability within an expected respiratory rate range can be used to determine a respiratory rate measurement.

In certain embodiments, the patient monitor 205 can obtain a respiratory rate measurement from variability detected in a patient's heart rate. The heart rate can be derived from an ECG signal, a bioimpedance signal, an acoustic signal, a plethysmograph signal, and/or combinations of the same.

In one embodiment, an instantaneous heart rate can be derived by determining the interval between successive R waves of the ECG signal and then converting the interval to beats per minute (bpm). For example, the heart rate can be calculated as 60 divided by the R-R interval in seconds. In another embodiment, the instantaneous heart rate can be derived from successive peaks in the plethysmograph signal. For example, the instantaneous heart rate can be calculated as 60 divided by the interval in seconds between the two successive peaks.

Other techniques can be used to derive the heart rate. For instance, the heart rate can be determined by analyzing any successive landmark of an ECG or plethysmograph signal. Further, to improve noise immunity, the patient monitor 205 can use a more robust technique to measure the interval, such as autocorrelation of the ECG or plethysmograph waveform from one beat to the next. More generally, any technique for reliably measuring the period from one beat to the next can be used.

The instantaneous heart rate can be plotted over time to illustrate variability in the patient's heart rate. In certain embodiments, the variability in the patient's heart rate is reflective of the patient's respiratory rate. For example, analysis of the variability in the instantaneous heart rate in the frequency domain (for example, by taking the Fourier transform of the instantaneous heart rate signal in the time domain) can provide an indication of respiratory rate that can be used to assess confidence in a respiratory rate measurement derived from an acoustic sensor or another type of sensor.

In certain embodiments, the patient monitor 205 can also obtain a respiratory rate measurement by measuring arterial pulse wave propagation time from the heart to an extremity. This propagation time is typically used by blood pressure monitoring systems and can be estimated by detecting a time difference between points on an ECG waveform and a photoplethysmograph waveform. This estimated propagation time is sometimes referred to as pulse wave transit time (PWTT) or time difference of arrival (TDOA). Currently available blood pressure monitoring systems trigger an automatic occlusive cuff to take a blood pressure measurement based on detected changes in PWTT.

Variability in the PWTT can be modulated by respiration. Thus, in certain embodiments, the patient monitor 205 can calculate PWTT and determine the variability in PWTT measurements over time. The patient monitor 205 can derive respiratory rate values from the calculated variability. The patient monitor 205 can use these values to improve the accuracy of or calculate confidence in acoustically-derived respiratory values.

Figure 3B:
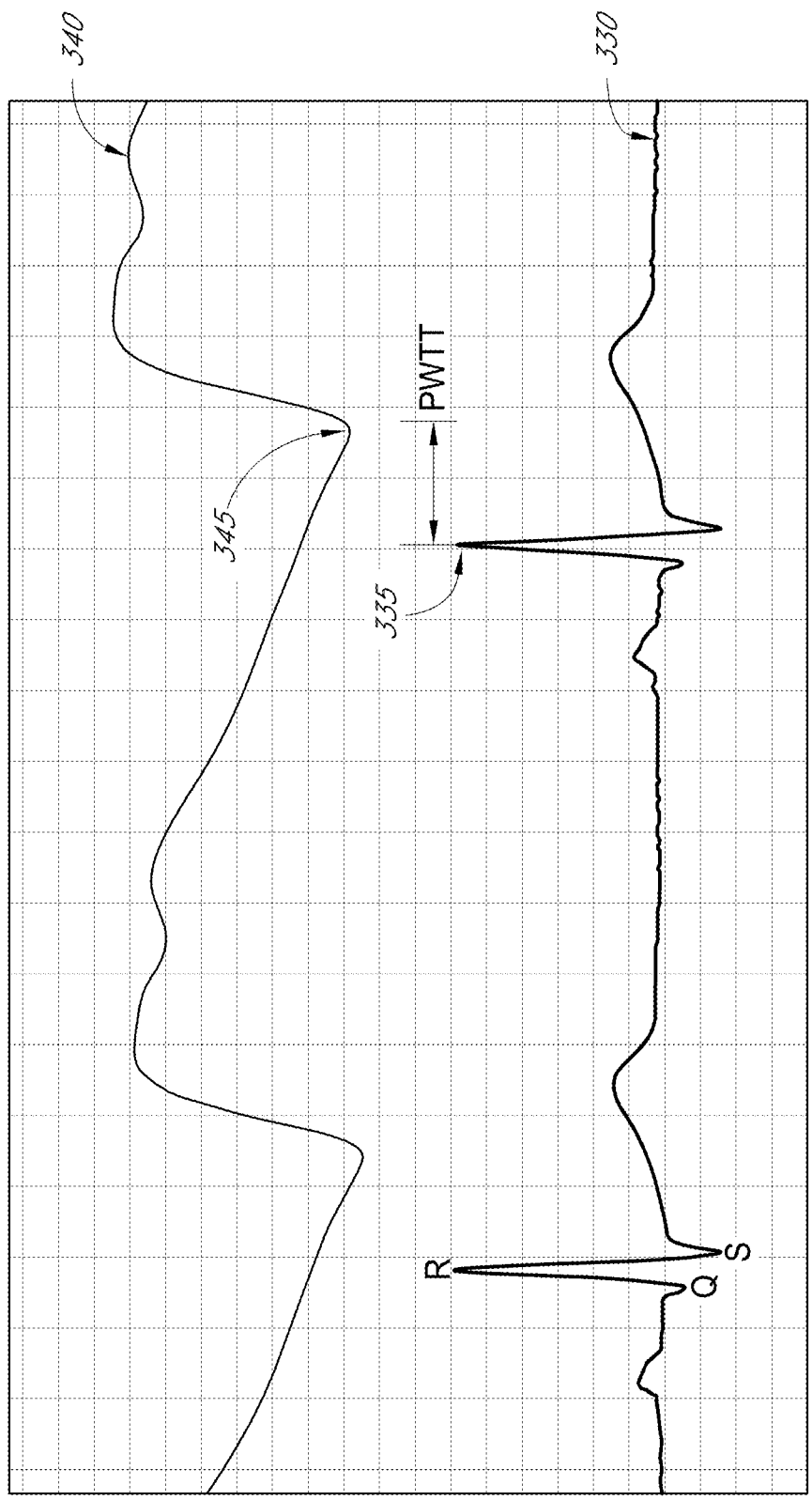
FIG. 3B schematically illustrates an example calculation of pulse wave transit time from two physiological signal inputs.

As illustrated in FIG. 3B, in one embodiment, PWTT is determined as a time difference between a peak of an R-wave 335 of a QRS complex of an ECG signal 330 to the foot point 345 of a plethysmograph signal 340. The R-wave 335 represents the first upward, or positive, deflection of the QRS complex and corresponds to the time of ventricular depolarization. The foot point 345 of the plethysmograph signal 340 can correspond to the time of earliest onset of arrival of the pulse at a location away from the heart (e.g., at a patient's finger). More generally, PWTT can be taken as a time interval from any feature of the ECG waveform to any feature of the pleth waveform. For example, PWTT can be taken as the interval between the Q or S points of the ECG waveform and a point such as the midpoint of the pleth waveform.

The PWTT calculation can be improved by accounting for a patient's pre-ejection period (PEP). The PEP can include the difference in time between initiation of ventricular contraction (e.g., as detected by an ECG) and ejection of blood from the ventricles into the aorta. The PEP can also be considered as an interval between the onset of the QRS complex (of an electrocardiogram) and cardiac ejection. PWTT compensated for PEP can more accurately represent the propagation time of the arterial pulse from the heart to an extremity. In order to determine the PEP, in one embodiment an acoustic sensor is coupled with the patient to detect a patient's heart sound. The time difference between a feature of the ECG signal and a feature of the heart sound (represented as a signal) can be an estimate of PEP. In another embodiment, a bioimpedance sensor can be used to estimate PEP by taking a time difference between features of ECG and bioimpedance sensor signals. The arterial PWTT can then be calculated by subtracting the PEP from the initial PWTT calculation obtained from the ECG and plethysmograph signals. The patient monitor 205 can employ any of the systems or methods for determining PWTT and PEP described in more detail in U.S. Provisional Application No. 61/366,862, titled "System for Triggering A Non-Invasive Blood Pressure Device," filed Jul. 22, 2010, the disclosure of which is hereby incorporated by reference in its entirety.

In yet other embodiments, the PWTT is determined from a landmark of a first plethysmograph signal to a landmark of a second plethysmograph signal. In some embodiments, the first plethysmograph signal is acquired from a sensor applied to a finger of a patient and the second plethysmograph signal is acquired from a sensor applied to a toe of a patient; however other sensor locations can be used as desired and/or required.

Figure 3C:
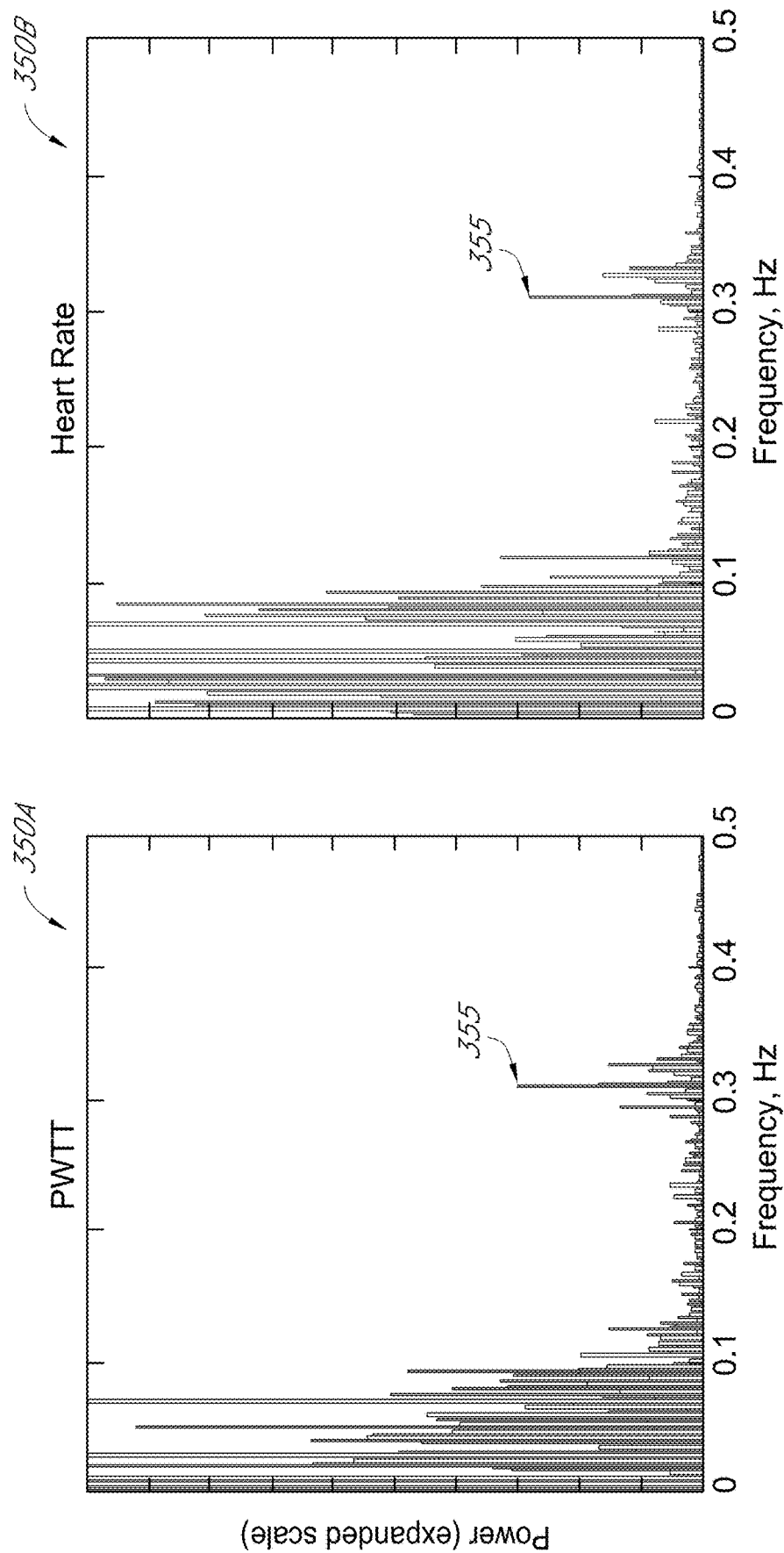
FIG. 3C illustrates example power spectrum plots of pulse wave transit time variability and heart rate variability for determining respiratory rate measurements.

The analysis of the heart rate and/or PWTT variability can include correlation in the time, frequency, or other transform domains. In one embodiment of a frequency domain analysis, FIG. 3C illustrates power spectrums 350A, 350B of the PWTT variability and the heart rate variability of a patient being monitored with the patient monitor 205. The power spectrums 350A, 350B plot power amplitude (having an expanded scale) versus frequency. In one embodiment, the respiratory rate measurement is determined from the power spectrums 350A, 350B by the highest spectral peak in the frequency range corresponding to the normal range of respiratory rates. The respiratory peak 355 of the power spectrums 350A, 350B is approximately 0.3 Hz, which corresponds to a respiratory rate of approximately 18 breaths per minute. This is an example frequency value that can vary for different patients or even for the same patient over time.

The respiratory rate measurement derived from the PWTT variability and the respiratory rate measurement from the heart rate variability can be compared with each other and/or with other respiratory rate measurements to determine an overall respiratory rate measurement or to assess confidence in a respiratory rate measurement derived from another physiological signal, as described in further detail below.

In certain embodiments, the PWTT and/or heart rate variability data can be smoothed or otherwise filtered by various signal processing methods, such as moving average smoothing, sliding average smoothing, box smoothing, binomial (Gaussian) smoothing, polynomial smoothing, and/or the like, to improve the accuracy of, or confidence in, the respiratory rate measurements.

Figure 4:
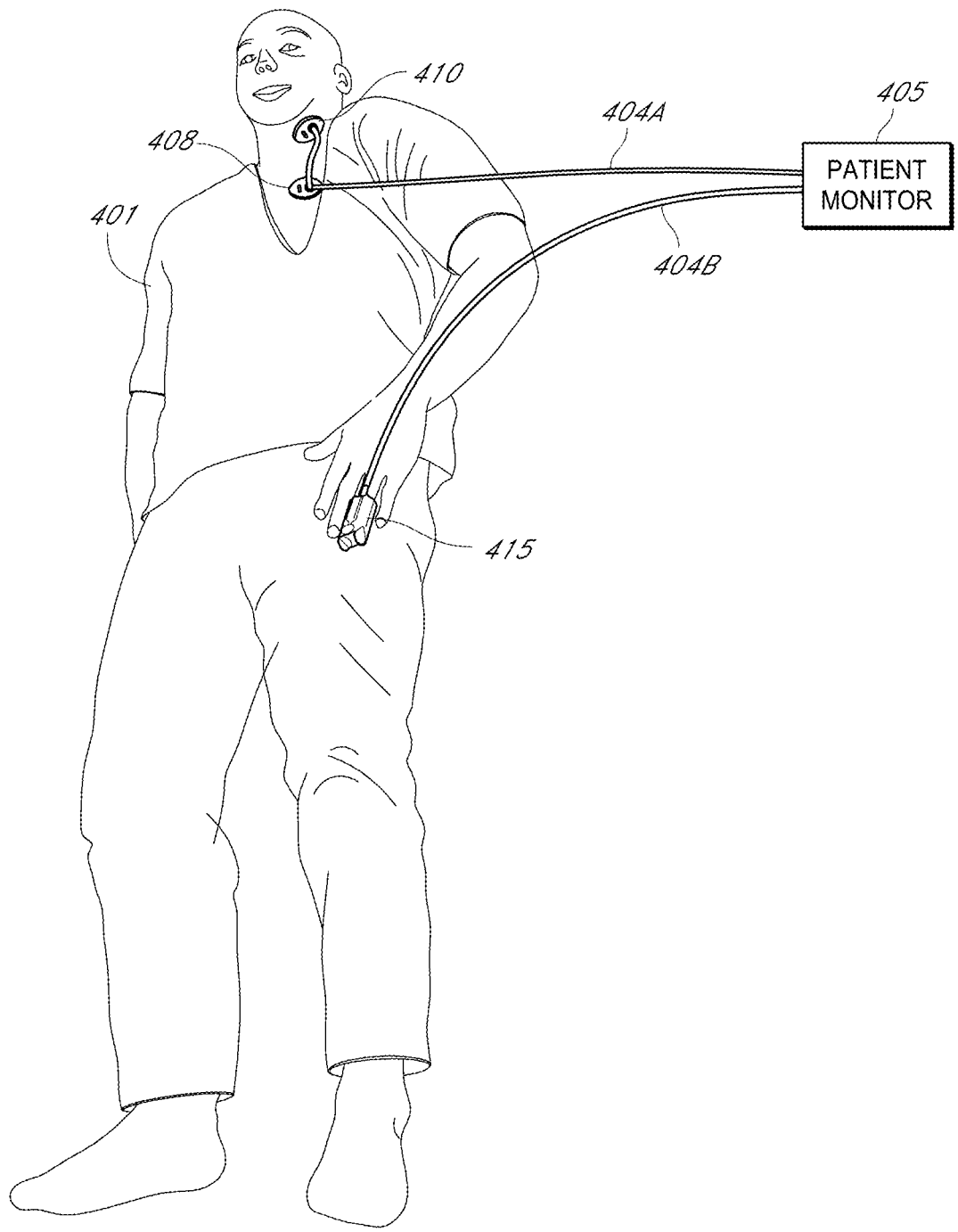
FIG. 4 illustrates an embodiment of the multiparameter patient monitoring system of FIG. 2 coupled to a patient.

FIG. 4 illustrates an embodiment of a multiparameter patient monitoring system 400 coupled to a patient 401. The multiparameter patient monitoring system 400 includes a patient monitor 405, an acoustic sensor 410, and an optical sensor 415. The acoustic sensor 410 and the optical sensor 415 can obtain physiological signals from the patient 401 and transmit the signals to the patient monitor 405 through cables 403A, 403B.

As shown, the acoustic sensor 410 is attached to the skin of the patient 401 on the neck near the trachea. The acoustic sensor 410 can include adhesive elements (e.g., tape, glue, or the like) to secure the acoustic sensor 410 to the skin. The acoustic sensor 410 can additionally be secured to the patient using an anchor 408, which can be affixed near a subclavian region of the patient 401 or at other regions. The anchor 408 can reduce stress on the connection between the acoustic sensor 410 and the skin during movement. Other placement locations for the acoustic sensor 410 and the patient anchor 408 are also possible, such as other parts of the neck, the chest, or the like.

The optical sensor 415 can be removably attached to the finger of the patient 401. In other embodiments, the optical sensor 415 can be attached to a toe, foot, and/or ear of the patient 401. The optical sensor 415 can include a reusable clip-type sensor, a disposable adhesive-type sensor, a combination sensor having reusable and disposable components, or the like. Moreover, the optical sensor 415 can also include mechanical structures, adhesive or other tape structures, Velcro™ wraps or combination structures specialized for the type of patient, type of monitoring, type of monitor, or the like.

In certain embodiments, the various sensors and/or monitors can communicate with the patient monitor 405 wirelessly. The wireless communication can employ any of a variety of wireless technologies, such as Wi-Fi (802.11x), Bluetooth, cellular telephony, infrared, RFID, combinations of the same, and the like.

Figure 5:
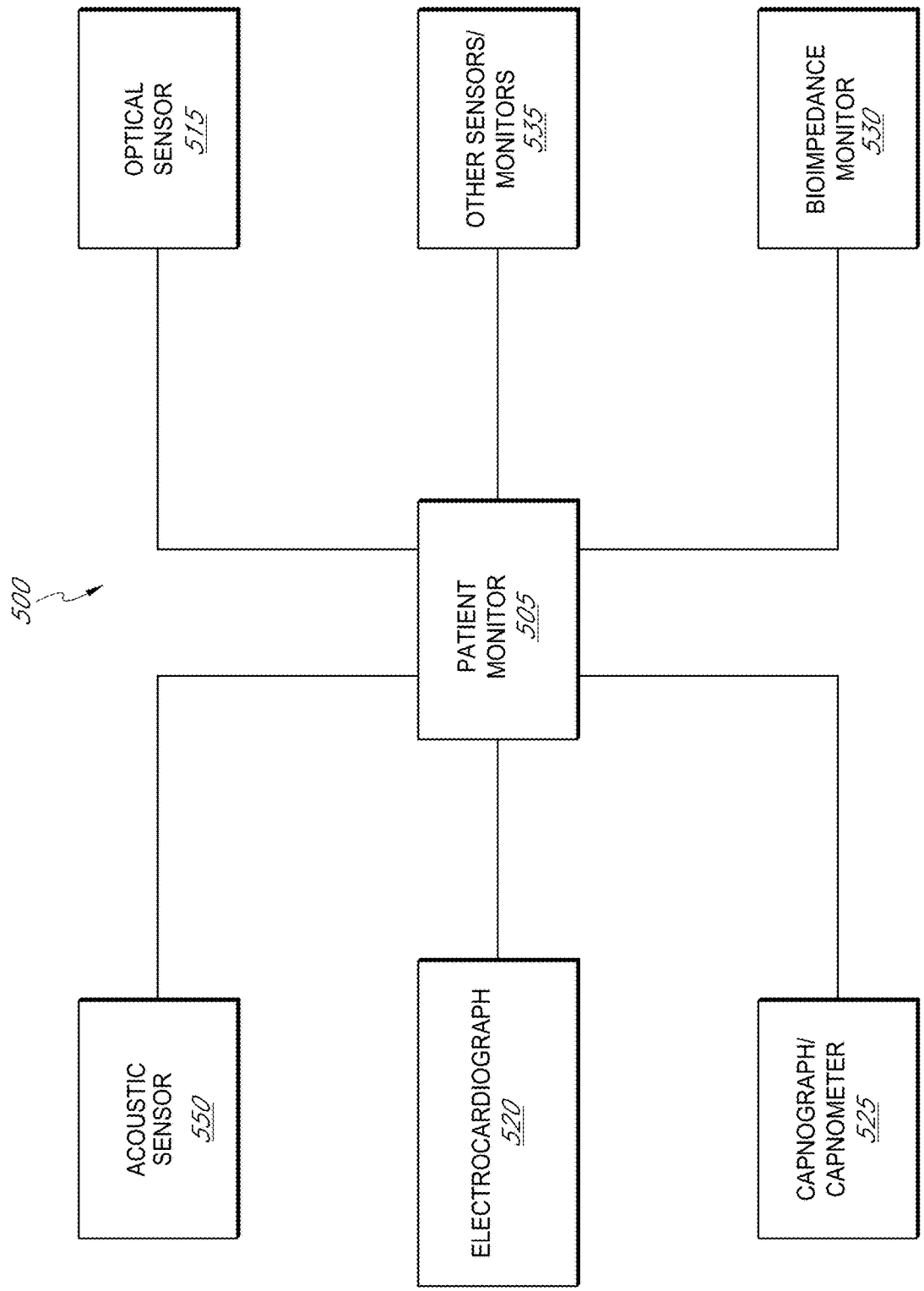
FIG. 5 illustrates a block diagram of an embodiment of a multiparameter patient monitoring system.

In certain embodiments, the multiparameter patient monitoring system 200 can include additional physiological parameter measurement devices. FIG. 5 illustrates an example of a multiparameter respiratory monitoring system 500 that includes multiple additional measurement devices. In particular, a patient monitor 505 receives inputs from an acoustic sensor 510, an optical sensor 515, an electrocardiograph (ECG) 520, a capnograph 525, a bioimpedance monitor 530, and possibly other physiological monitors or sensors 535.

In certain embodiments, the multiparameter patient monitor 505 derives respiratory rate measurements from signals received from each of the depicted physiological parameter measurement devices and/or sensors. In certain embodiments, the respiratory rate measurements derived from one or more of the optical sensor 515, the ECG 520, the capnograph 525, and/or the bioimpedance monitor 530 can be compared with the respiratory rate measurement from the acoustic sensor 510. The monitor 505 can compare one or more of these measurements with the acoustically-derived measurement in order to derive a multiparameter confidence value reflecting a confidence in the acoustic respiratory rate measurement (or confidence in any other of the respiratory rate measurements).

In other embodiments, one or more of the respiratory rate measurements from the ECG 520, the capnograph 525 and the bioimpedance monitor 530 can be combined with the respiratory rate measurements from the acoustic sensor 510 and/or the optical sensor 515 to generate a combined respiratory rate output. In certain embodiments, the combined respiratory rate output can have greater accuracy than the respiratory rate measurement obtained from any one of the devices shown.

The ECG 520 can monitor electrical signals generated by the cardiac system of a patient. The ECG 520 can include one or more sensors adapted to be attached to the skin of a patient, which can be used to detect electrical heart activity of the patient. The ECG 520 can determine any of a variety of electrical physiological parameters based upon electrical signals received from the one or more sensors, such as heart rate. In certain embodiments, the ECG 520 can generate an electrocardiogram waveform. The patient monitor 505 can compare one or more features of the waveform with an acoustically-derived respiratory rate measurement to determine multiparameter confidence in the acoustically-derived respiratory rate. For instance, the R-R time period of the ECG waveform, or the like can be correlated with respiratory rate in certain individuals. More generally, an envelope of the ECG waveform can include peaks that the patient monitor 505 can correlate in frequency with respiratory rate in certain situations.

The capnograph 525 can determine the carbon dioxide content in inspired and/or expired air from a patient. For example, the capnograph 525 can monitor the inhaled and/or exhaled concentration or partial pressure of carbon dioxide through a breathing mask or nasal cannula. In certain embodiments, the capnograph 525 can generate a capnogram responsive to the patient's breathing. The capnograph 525 can also identify end tidal carbon dioxide ($EtCO_2$) levels and/or other values. From the $EtCO_2$ values, the capnograph 525 can determine a respiratory rate of the patient. The capnograph 525 can provide this respiratory rate measurement to the patient monitor 505, which can compare the respiratory rate with the acoustically-derived respiratory rate to determine multiparameter confidence.

The bioimpedance monitor 530 can determine electrical impedance or resistance in body tissue of a medical patient. For example, the bioimpedance monitor 530 can include two or more sensors or electrodes positioned on a patient so as to measure the bioelectrical impedance or resistance across the chest region. The measured bioelectrical impedance can vary as a result of the expansion of the chest due to breathing, and from this variance, a respiratory rate measurement can be derived. In certain embodiments, the bioimpedance monitor 530 is a Transthoracic Impedance Monitor or the like, having two or more electrodes that can optionally be combined with ECG electrodes. In other embodiments, the bioimpedance monitor 530 is an impedance tomograph, having many more electrodes that can also be used to form a spatial image of the impedance variation.

The respiratory rate measurement can be derived by the bioimpedance monitor 530, or alternatively, the bioimpedance monitor 530 can provide impedance values with respect to time to the patient monitor 505, which can derive the respiratory rate. The patient monitor 505 can also compare the impedance-derived respiratory rate with the acoustically-derived respiratory rate to determine multiparameter confidence.

Additional sensors and/or monitors of different types can also be included. The other patient monitors 135 can include, for example, thermistor-based breathing sensors or pneumatic breathing belt sensors.

In certain embodiments, the electrocardiograph 520, the capnograph/capnometer 525, and the bioimpedance monitor 530 are standalone patient monitors that can provide filtered and/or processed signals to the patient monitor 505. In other embodiments, the electrocardiograph 520, the capnograph 525, and the bioimpedance monitor 530 can be replaced with respective sensors, which each provide physiological data directly to the patient monitor 505. In still other embodiments, the acoustic sensor 510 and the optical sensor 515 can be replaced with an acoustic respiratory monitor and a pulse oximeter, respectively. Thus, any combination of sensors and monitors can provide inputs to the patient monitor 505, including any subset of the devices shown.

The patient monitor 505 can output for display the respiratory rate value derived from the acoustic sensor 550. In addition, the patient monitor 505 can output respiratory rate values derived from any of the other devices shown.

In certain embodiments, the respiratory rate measurements derived from one or more of the sensors can be used for sequential hypothesis testing.

Figure 6A:
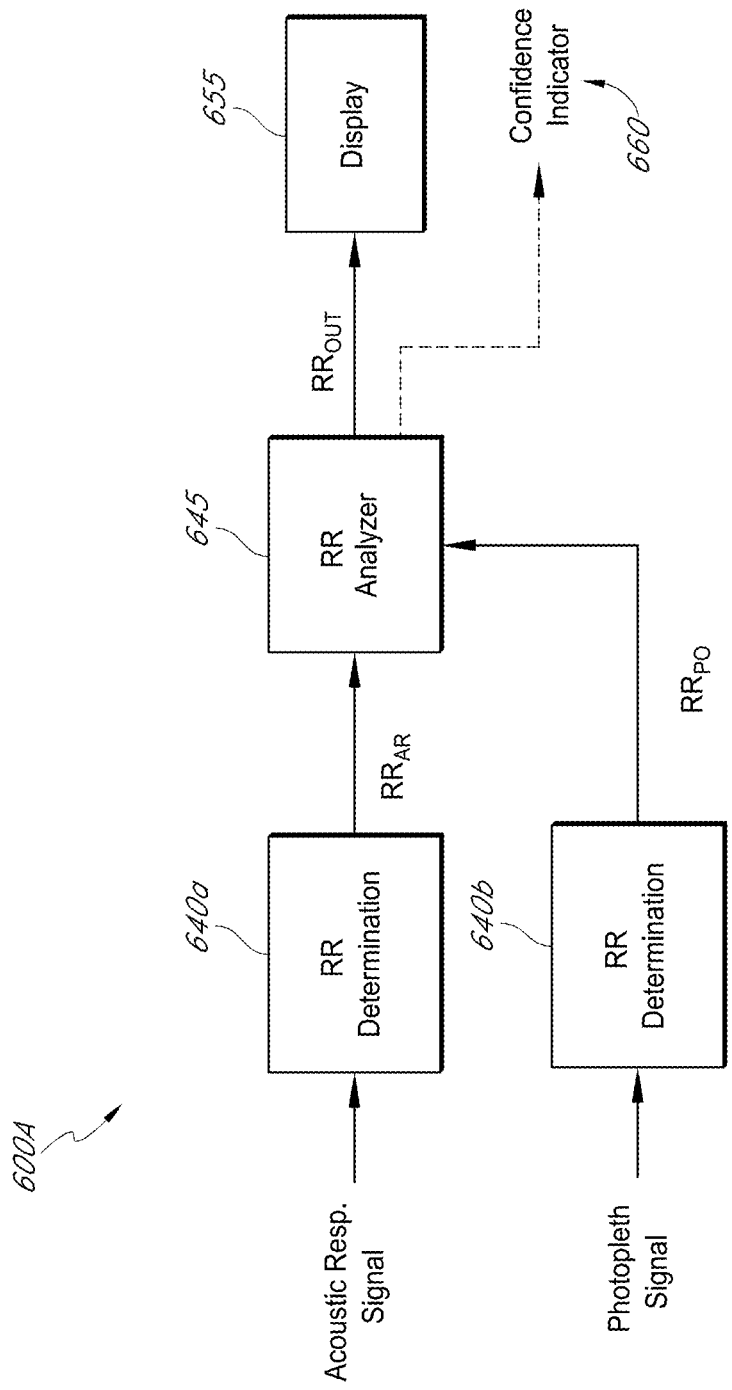
Figure 6C:
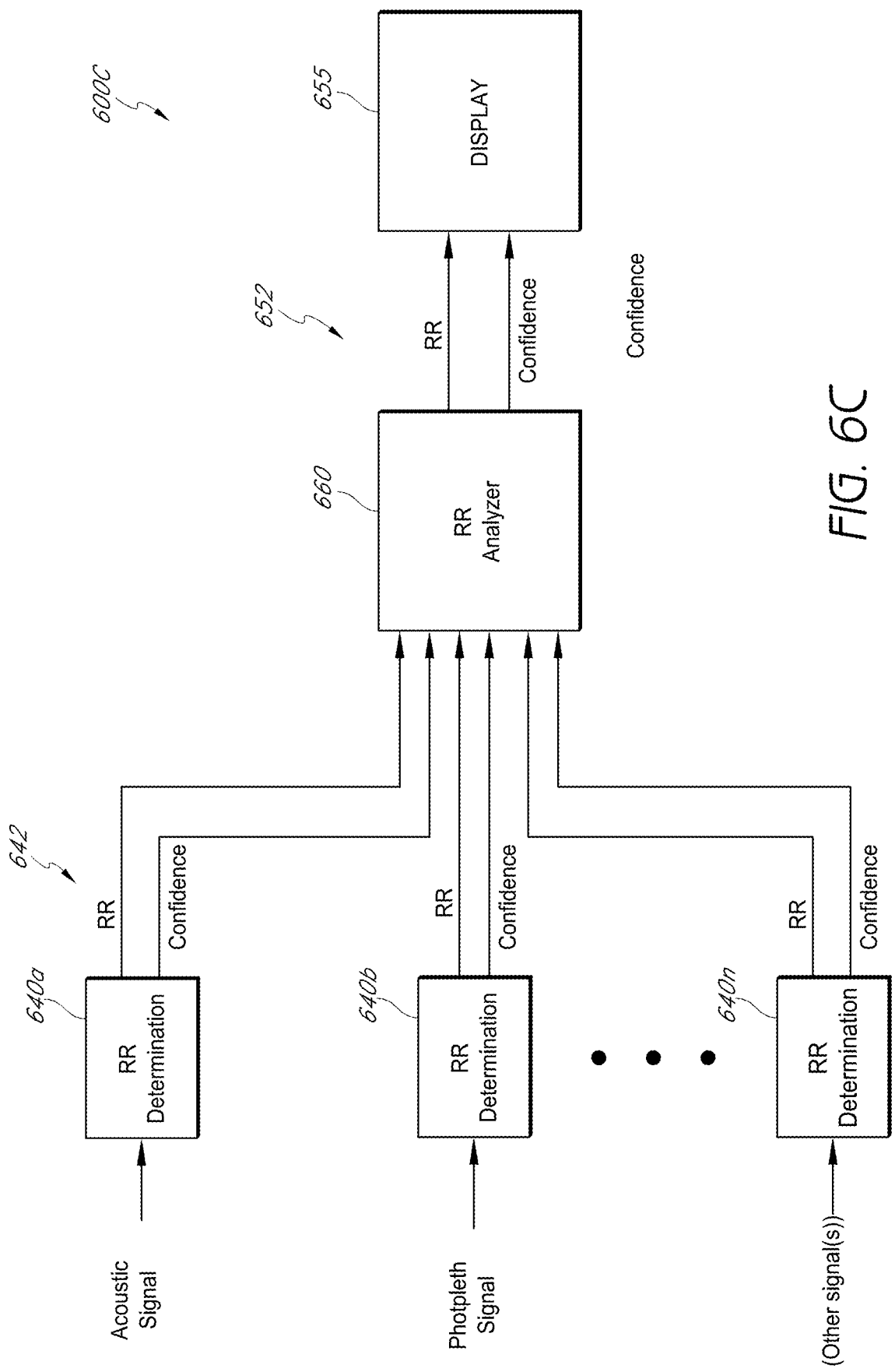

FIGS. 6A through 6C illustrate embodiments of systems 600A, 600B, and 600C for determining multiparameter confidence of respiratory rate measurements and for outputting respiratory rate values. The systems 600A, 600B, and 600C can be implemented by any of the patient monitors described herein, such as the patient monitors 205, 405, and 505, or by the patient monitors described below. Each of the depicted blocks of the systems 600A, 600B, and 600C can be implemented by hardware and/or software.

Referring to FIG. 6A, the system 600A receives signal inputs reflective of physiological parameters from an acoustic sensor and from an optical sensor, such as any of the sensors described above. The signal inputs can be received by respiratory rate determination blocks 640a, 640b, respectively. Each of the respiratory rate determination blocks 640 can determine a respiratory rate based at least in part on its respective signal input. For example, the respiratory rate determination block 640b can determine respiratory rate of a patient from a time domain or frequency analysis of a photopleth input signal.

In certain embodiments, the respiratory rate determination block 640b can be part of any of the patient monitors described above. Thus, for example, an optical sensor could provide the photopleth signal to the respiratory rate determination block 640b of a patient monitor, which derives a respiratory rate. The respiratory rate determination block 640b could instead be part of a pulse oximetry monitor. The pulse oximetry monitor could determine a respiratory rate measurement based at least in part on the photopleth signal. The pulse oximetry monitor could provide the calculated respiratory rate to the patient monitor (e.g., 205, 405, 505, or the like).

For convenience, the acoustic respiratory rate measurement will be described using the shorthand $RR_{AR}$ and the photopleth respiratory rate measurement will be described using the shorthand $RR_{PO}$. In the depicted embodiment, the $RR_{AR}$ and the $RR_{PO}$ measurements are provided to a respiratory rate analyzer 645. The respiratory rate analyzer 645 can analyze the $RR_{AR}$ and the $RR_{PO}$ measurements to determine a multiparameter confidence in the $RR_{AR}$ measurement. For example, the respiratory rate analyzer 645 can compare the two measurements to determine a difference between the two measurements. The respiratory rate analyzer can derive a multiparameter confidence or multiparameter confidence value from this calculated difference. In certain embodiments, the greater the difference between the $RR_{AR}$ and the $RR_{PO}$ measurements, the lower is the multiparameter confidence determined for the $RR_{AR}$ measurement. Conversely, in certain embodiments, the respiratory rate analyzer 645 can use the difference between the two measurements to assign a multiparameter confidence to the $RR_{PO}$ measurement.

The respiratory rate analyzer 645 can output for display a multiparameter confidence indicator 660 responsive to the calculated multiparameter confidence along an output respiratory rate measurement ($RR_{OUT}$, described below). The multiparameter confidence indicator 660 can include a visual and/or audible indication in various embodiments.

Moreover, in certain embodiments, the respiratory rate analyzer 645 can generate the respiratory rate output $RR_{OUT}$ based on a combination of the inputs $RR_{AR}$ and $RR_{PO}$. For example, the respiratory rate analyzer 645 could average the two respiratory rate inputs. This average could be a weighted average or the like (see, e.g., FIG. 6C).

In another embodiment, the respiratory rate analyzer selects one of the respiratory rate inputs ($RR_{AR}$ and $RR_{PO}$) to output as the respiratory rate output $RR_{OUT}$. The respiratory rate analyzer 645 could make this selection based at least partly on single parameter confidence values generated by each respiratory rate determination block 640a, 640b. These single parameter confidence values can reflect a quality of the signal received by each block 640a, 640b. Single parameter confidence values can be distinguished from multiparameter confidence values, in certain embodiments, in that single parameter confidence values can reflect confidence that a respiratory rate derived from a single parameter is accurate. In contrast, multiparameter confidence values can reflect respiratory rate accuracy as determined by an analysis of multiple parameters (e.g., photopleth and ECG).

For example, the respiratory rate determination block 640b could determine single parameter confidence of the photopleth signal using techniques such as those described in U.S. Pat. No. 6,996,427, titled "Pulse Oximetry Data Confidence Indicator," filed Dec. 18, 2003, (the "'427 patent") the disclosure of which is hereby incorporated by reference in its entirety. Analogous techniques could be used by the respiratory rate determination block 640a to determine single parameter confidence in the quality of the acoustic respiratory signal received.

The respiratory rate analyzer 645 could select either the $RR_{AR}$ respiratory rate value or the $RR_{PO}$ respiratory rate value to provide as the respiratory rate output $RR_{OUT}$ based on, for example, which signal has a higher calculated signal quality. In another embodiment, the respiratory rate analyzer 645 could weight a combination of the two respiratory rate values based at least in part on the single parameter confidence values. In various embodiments, the respiratory rate analyzer 645 can also select the respiratory rate value to output based on patient-specific factors, such as age, gender, comorbidity, and the like. For instance, for some patients, one respiratory rate measurement derived from a particular parameter might be more reliable than other respiratory rate measurements derived from other parameters. Many other variations are also possible.

Although the respiratory rate analyzer 645 has been described as being able to average respiratory rate values or select respiratory rate values, the distinction between averaging and selecting can blur. Selecting, for instance, can be considered a subset of weighting where respiratory rate values selected are given a weight of "1" (or substantially 1) and respiratory rate values not selected are given a weight of "0" (or substantially 0).

FIG. 6B extends the embodiment shown in FIG. 6A to include additional parameter inputs. In FIG. 6B, the system 600B receives an acoustic respiratory signal, a photopleth signal, an ECG signal, a capnograph signal, and a bioimpedance signal. Signal inputs from other types of sensors and/or monitors, or additional sensors of the types listed, can also be received. The respective signal inputs are received by respiratory rate determination blocks 640a, 640b, 640c, 640d, and 640e. As described above, the respiratory rate determination blocks 640a, 640b can determine a respiratory rate measurement using any of the techniques described above and optionally a single parameter confidence value based at least in part on its respective signal input. Likewise, the respiratory rate determination blocks 640c, 640d, and 640e can calculate respiratory rate measurements and optionally single parameter confidence values.

Signal inputs can also be used to determine respiratory rate measurements derived from heart rate variability and/or PWTT variability. As shown in FIG. 6B, the signal inputs (e.g., an acoustic respiratory signal, a photopleth signal, an ECG signal, a bioimpedance signal and/or other signals) are received by a heart rate determination block 670 and a PWTT determination block 675. In other embodiments, more or fewer signal inputs can be received by the heart rate determination block 670 and/or the PWTT determination block 675. The heart rate determination block 670 can derive the patient's heart rate from one or more of the signal inputs. The PWTT determination block 675 can determine the patient's PWTT from one or more of the signal inputs using any of the techniques described above with respect to FIG. 3B.

The respiratory rate determination blocks 640f and 640g can determine respiratory rate measurements based at least in part on an analysis of the heart rate variability and the PWTT variability, respectively, of the patient, using any of the techniques described above. For example, the respiratory rate determination blocks 640f and 640g can determine respiratory rate measurements from a frequency analysis of heart rate and/or PWTT signals over time. The respiratory rate measurements calculated by the respiratory rate determination blocks 640f and 640g can be provided to the respiratory rate analyzer 650 along with any of the respiratory rate measurements calculated by the respiratory rate determination blocks 640a, 640b, 640c, 640d and 640e. The respiratory rate determination blocks 640f and 640g can also calculate single or multiple parameter confidence values.

The respiratory rate determination blocks 640 can be implemented in any of the patient monitors 205, 405, 505, etc. described herein. Thus, for example, a patient monitor can receive sensor inputs from one or more of an acoustic sensor, an optical sensor, an ECG sensor or sensors, a capnometry sensor, and a bioimpedance sensor. Not all of the inputs shown need by received by a patient monitor; rather, a subset can be received by any patient monitor. From the inputs, the patient monitor implementing the respiratory rate determination blocks 640 can calculate individual respiratory rate measurements corresponding to each input, using any of the techniques described above. The patient monitor can further implement the respiratory rate determination blocks 640 by calculating single parameter confidence in each block in an analogous manner to that described in the '427 patent incorporated by reference above. In another embodiment, the respiratory rate calculation for certain of the parameters is performed in a separate monitor. For instance, a capnograph monitor can determine a respiratory rate of a patient and provide this respiratory rate value to a respiratory rate analyzer 650 of the patient monitor.

The respiratory rate determination blocks 640 can provide respiratory rate values and optionally single parameter confidence values to a respiratory rate analyzer 650. The respiratory rate analyzer 650 can operate in a similar manner to the respiratory rate analyzer 645 described above. For instance, the respiratory rate analyzer 650 can analyze one or more of the respiratory rate measurements to determine a multiparameter confidence in the $RR_{ARM}$ measurement, using any of the techniques described above.

In one embodiment, the respiratory rate analyzer 650 determines multiparameter confidence by comparing the $RR_{AR}$ measurement to one or more of the other respiratory rate measurements. The multiparameter confidence calculated by the respiratory rate analyzer 650 can reflect the differences between the measurements. For example, the respiratory rate analyzer 650 can average the differences to generate a multiparameter confidence value, use a weighted average of the differences to generate a multiparameter confidence value, can select the greatest difference as the multiparameter confidence value, can use any of the above to further derive a multiparameter confidence value (e.g., by looking up the difference value in a look-up table to obtain a corresponding multiparameter confidence value, or by multiplying the difference value by a scalar to obtain a multiparameter confidence value), or by a host of other techniques. Moreover, in certain embodiments, the respiratory rate analyzer 650 can analyze any subset of the respiratory rate measurements received to determine a multiparameter confidence in any given one of the respiratory rate measurements.

The respiratory rate analyzer 650 can output for display a multiparameter confidence indicator 660 responsive to the calculated multiparameter confidence along an output respiratory rate measurement ($RR_{OUT}$, described below). The multiparameter confidence indicator 660 can include a visual and/or audible indication in various embodiments. The multiparameter confidence indicator 660 can be output to a display 655 along with a respiratory rate output $RR_{OUT}$.

Moreover, like the respiratory rate analyzer 645 described above, the respiratory rate analyzer 650 can generate the respiratory rate output $RR_{OUT}$ based on a combination or selection of any of the respiratory rate inputs received from the various sensors or monitors. For example, the respiratory rate output $RR_{OUT}$ can be the acoustic respiratory rate ($RR_{AR}$), or a selected one of the other respiratory rate measurements. Or, the respiratory rate analyzer 650 could average, perform a weighted average (e.g., based on respective single parameter confidences), or otherwise combine the respiratory rate measurements to determine the respiratory rate output $RR_{OUT}$. In various embodiments, the respiratory rate analyzer 645 can also select and/or combine the respiratory rate values to determine an output based on patient-specific factors, such as age, gender, comorbidity, and the like. For instance, for some patients, one respiratory rate measurement derived from a particular parameter might be more reliable than other respiratory rate measurements derived from other parameters. Many other variations are also possible.

In other embodiments, the combiner/selector module 650 can compare the derived respiratory rate measurements to determine, which, if any, of the respiratory rate determination blocks 640 provided outliers. The combiner/selector module 650 could reject the outliers and combine (e.g., average) the outputs of the remaining respiratory rate determination blocks 640.

In yet other embodiments, the combiner/selector module 650 could determine which of the outputs from the respiratory rate determination blocks 640 are close to each other (e.g., within a tolerance) and output a combination of those outputs. For example, if three of the five respiratory rate determination blocks 640 produce a similar output and two are outliers, the combiner/selector module 650 could average the three similar outputs or select one of the three outputs as the final $RR_{OUT}$ measurement. Moreover, the combiner/selector module 650 can learn over time and can select the output derived from one of the sensors or monitors based on past performance. Many other configurations and extensions of the combiner/selector module 650 are possible.

In certain embodiments, the respiratory rate output measurements and/or the multiparameter confidence values can be output to an external device over a network, instead of, or in addition to, being output to the display 655. For example, the output data can be output to a central monitoring station (such as a nurses' monitoring station), a server, a laptop computer, a cell phone, a smart phone, a personal digital assistant, other patient monitors, or other clinician devices, for example. In some embodiments, the patient monitor 505 can transmit data to an external device via a wireless network using a variety of wireless technologies, such as Wi-Fi (802.11x), Bluetooth, cellular telephony, infrared, RFID, combinations of the same, and the like.

FIG. 6C illustrates yet another embodiment of a system 600C for calculating multiparameter confidence in respiratory rate measurements. In the system 600C, acoustic and photopleth signal inputs are provided, as well as optionally any number of other signal inputs (such as any of the inputs described above). As above, respiratory rate determination blocks 640a, 640b, and so forth down to 640n can receive these signal inputs. The respiratory rate determination blocks 640a, 640b, . . . , 640n can calculate respiratory rate values based on the signal inputs, as well as associated internal confidence values. Each of the internal confidence values can reflect an individual respiratory rate block 640 algorithm's confidence in the respiratory rate measurements.

A respiratory rate analyzer 660 receives the respiratory rate and confidence measurements 642 calculated by the respiratory rate determination blocks 640. The respiratory rate analyzer 660 can have some or all the features of the respiratory rate analyzers described above. In addition, the respiratory rate analyzer 660 can use the internal confidence values calculated by the respiratory rate blocks 640 to weight, select, or otherwise determine appropriate overall respiratory rate and confidence values 652. The respiratory rate analyzer 660 outputs these values 652 to a display 655 or to some other device.

The respiratory rate analyzer 660 can use any of a variety of techniques to calculate the overall respiratory rate and confidence 652. Some example techniques are described herein. To illustrate, in one embodiment, the respiratory rate analyzer 660 can perform a weighted average of the respiratory rate values from each respiratory rate determination block 640. The weights can be derived from, or can be, their respective confidence values.

More complex weighting schemes can also be devised. One example weighting algorithm can implement an adaptive algorithm for dynamically adjusting the weights applied to each respiratory rate value over time. The weights can be adapted based on minimizing some cost function, such as may be applied by a Kalman filter, for instance. More generally, any of a variety of adaptive algorithms may be used to adjust the weights. For example, the respiratory rate analyzer 660 can implement one or more of the following: a least mean squares algorithm (LMS), a least squares algorithm, a recursive least squares (RLS) algorithm, wavelet analysis, a joint process estimator, an adaptive joint process estimator, a least-squares lattice joint process estimator, a least-squares lattice predictor, a correlation canceller, optimized or frequency domain implementations of any of the above, any other linear predictor, combinations of the same, and the like.

In another embodiment, the respiratory rate analyzer 660 can select the top N available sources having the highest confidence level, where N is an integer. For instance, the respiratory rate analyzer 660 can choose the output of N respiratory rate determination blocks 640 having confidence values that exceed a threshold. This threshold may be determined relative to the confidence values provided (e.g., via a ratio or the like) or can be an absolute threshold. The respiratory rate analyzer 660 can then perform a weighted average of the remaining values or select from these values, for example, based on confidence values.

Internal confidence of each respiratory rate determination block 640 can depend on a variety of factors, such as signal to noise ratio, irregularities in the data, probe-off conditions, and the like. A probe off condition, for instance, can result in a zero confidence value, a gradual taper down to zero confidence over time, or the like. Likewise, the confidence values can be derived from the signal to noise ratio for each respiratory rate determination block 640.

Figure 7:
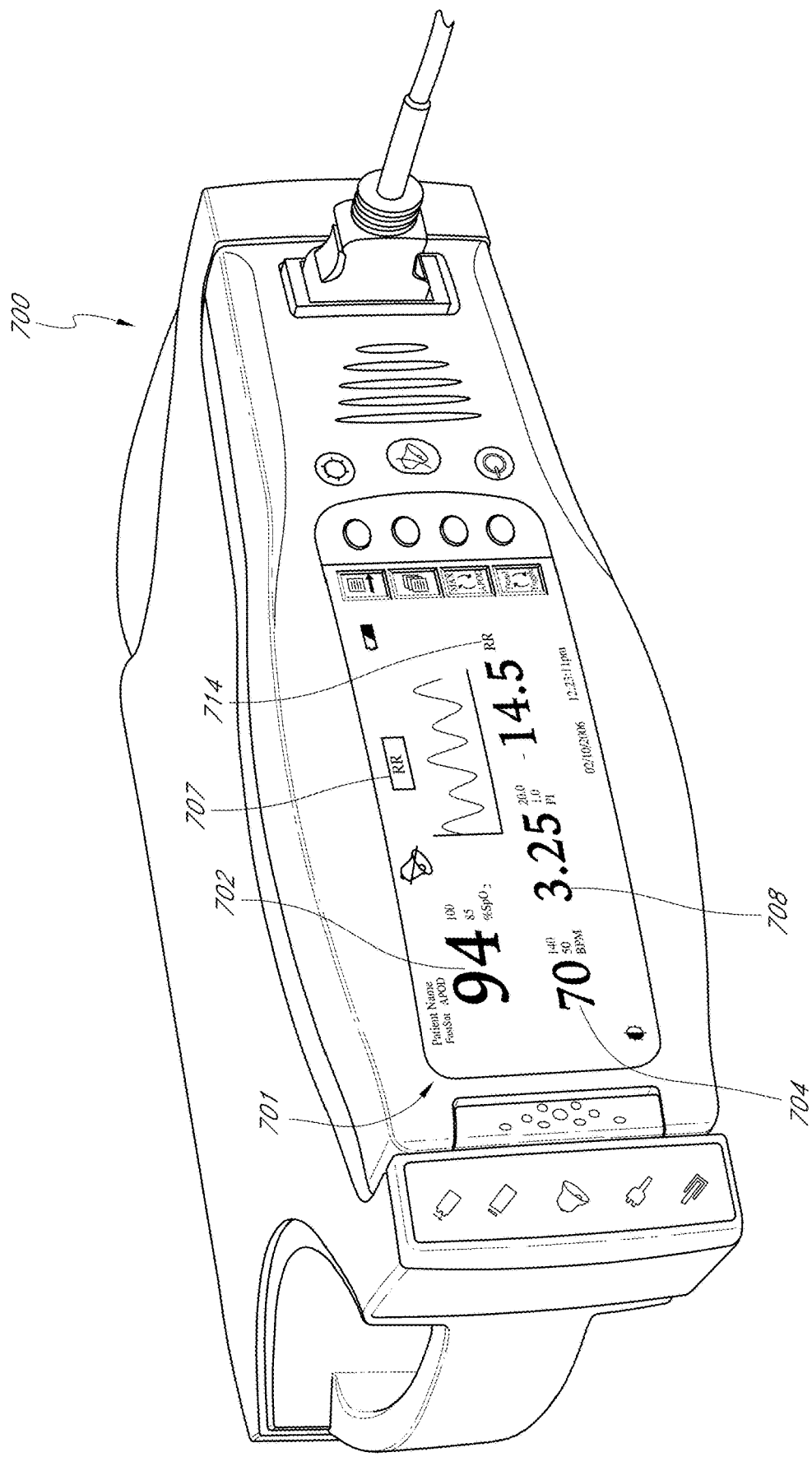
FIG. 7 illustrates an example multiparameter physiological monitor.

FIG. 7 illustrates an example noninvasive multiparameter physiological monitor 700 that can implement any of the features described herein. An embodiment of the monitor 700 includes a display 701 showing data for multiple physiological parameters. For example, the display 701 can include a CRT or an LCD display including circuitry similar to that available on physiological monitors commercially available from Masimo Corporation of Irvine, Calif. sold under the name Radical™, and disclosed in U.S. Pat. Nos. 7,221,971; 7,215,986; 7,215,984 and 6,850,787, for example, the disclosures of which are hereby incorporated by reference in their entirety. However, many other display components can be used that are capable of displaying respiratory rate and other physiological parameter data along with the ability to display graphical data such as plethysmographs, respiratory waveforms, trend graphs or traces, and the like.

The depicted embodiment of the display 701 includes a measured value of respiratory rate 712 (in breaths per minute (bpm)) and a respiratory rate waveform graph 706. In addition, other measured blood constituents shown include $SpO_2$ 702, a pulse rate 704 in beats per minute (BPM), and a perfusion index 708. Many other blood constituents or other physiological parameters can be measured and displayed by the multiparameter physiological monitor 700, such as blood pressure, ECG readings, $EtCO_2$ values, bioimpedance values, and the like. In some embodiments, multiple respiratory rates, corresponding to the multiple input sensors and/or monitors, can be displayed.

Figure 8A:
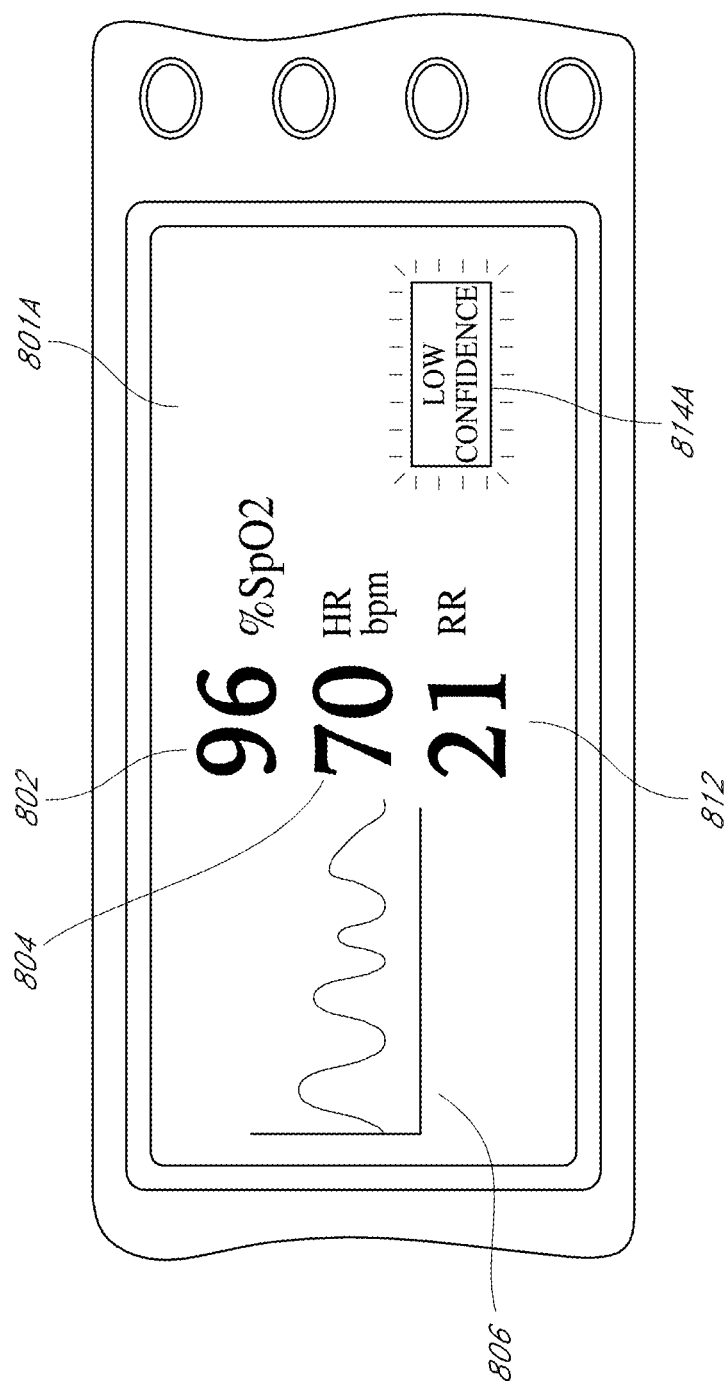
FIGS. 8A through 8D illustrate example multiparameter physiological monitor displays.
Figure 8B:
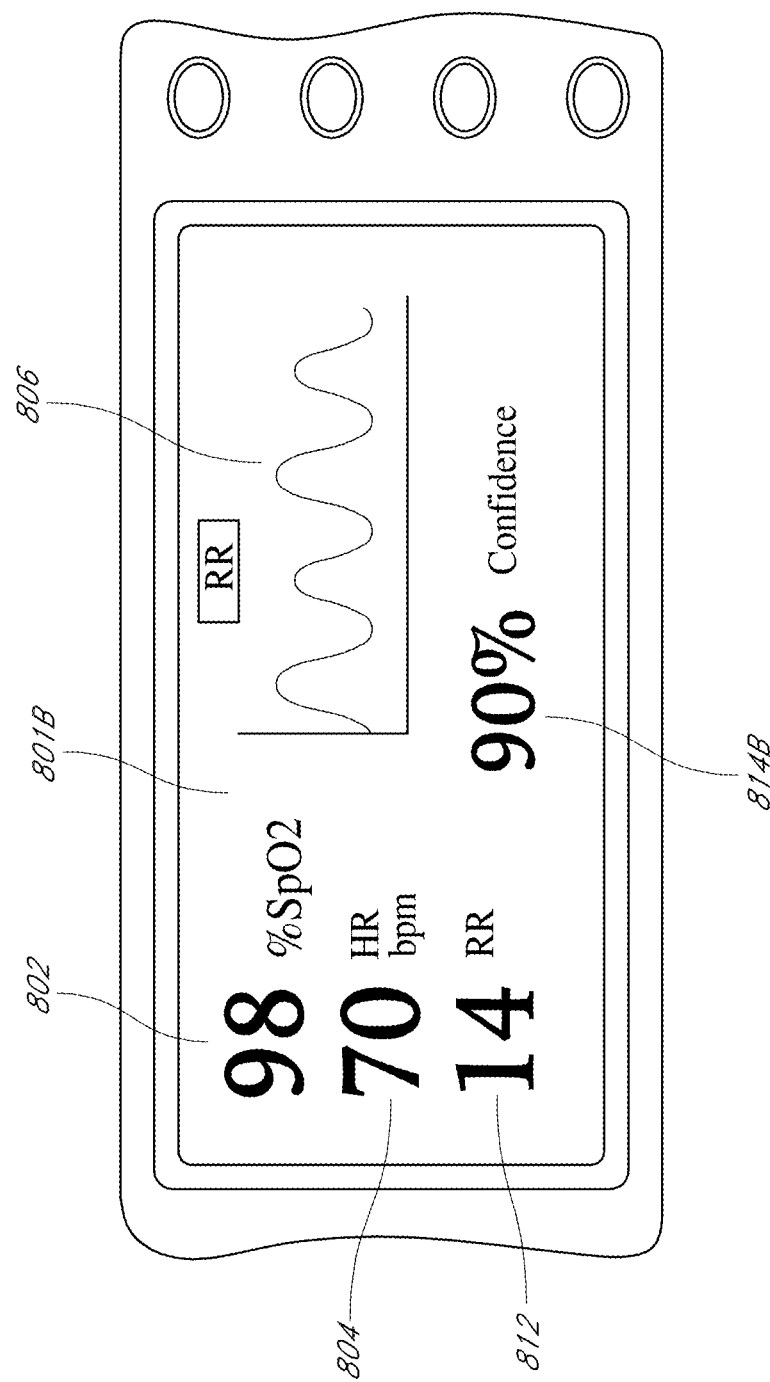
Figure 8C:
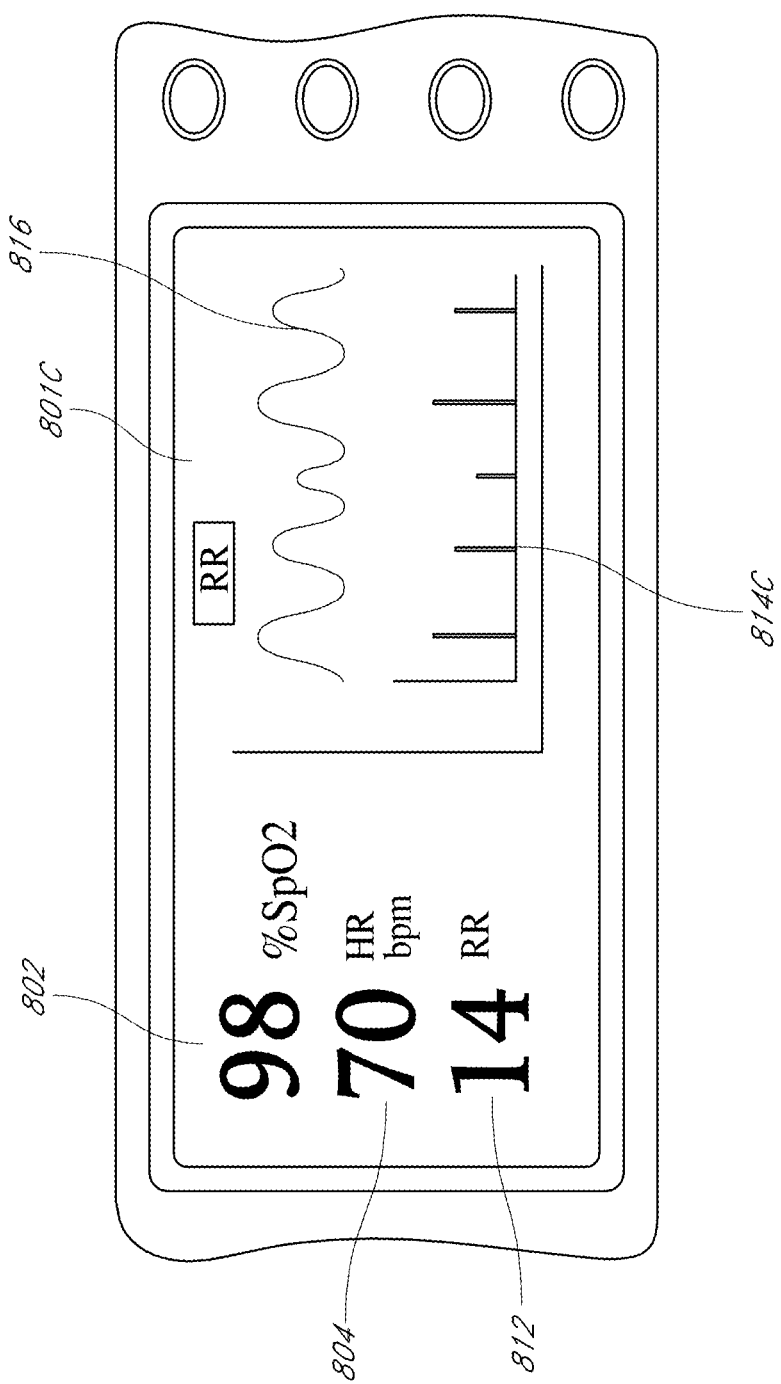

FIGS. 8A through 8C illustrate example multiparameter physiological monitor displays 801A-801C that output multiparameter confidence indicators 814. The multiparameter confidence indicators 814 can be generated using any of the techniques described above.

Referring to FIG. 8A, an example display 801A is shown that includes parameter data for respiratory rate, including a measured respiratory rate value 812 in breaths per minute (bpm) and a respiratory waveform graph 806. The display 801A also includes parameter data for $SpO_2$ 802 and pulse rate 804 in beats per minute (BPM). A respiratory rate multiparameter confidence indicator 814A is also depicted. In the depicted embodiment, the multiparameter confidence indicator 814A includes text that indicates that the current respiratory rate has a low multiparameter confidence level. The multiparameter confidence indicator 814A can function as a visual multiparameter confidence-based alarm by flashing, changing color, or the like when the multiparameter confidence is below a threshold level. The multiparameter confidence indicator can include symbols other than (or in addition to) text in certain embodiments. An audible multiparameter confidence-based alarm can alternatively, or additionally, be output through a speaker or other audio output device. A multiparameter confidence-based alarm can be generated as described in the '427 patent described above.

In certain embodiments, an alarm can be output when the monitored respiratory rate of the patient deviates beyond a patient-specific and/or patient-independent threshold. The utility and effectiveness of an alarm based on a respiratory rate measurement determined solely from an acoustic signal can be improved by joint processing of ancillary signals from multiple monitored physiological parameters, such as those described herein (e.g., electrical signals, photoplethysmographic signals, bioimpedance signals, and/or the like).

For example, respiratory rate measurements determined from the ancillary signals can be used to continuously or periodically refine or assess confidence in the respiratory rate measurements derived from the acoustic signal. If the multiparameter confidence in the acoustic respiratory rate measurement is low, the alarm can be suppressed, at least pending further consideration; however, if the multiparameter confidence in the acoustic respiratory rate measurement is sufficiently high, the alarm can be output without further consideration.

In other embodiments, the ancillary signals can be used to estimate the initial respiratory rate or timing information to assist an acoustic signal processing algorithm in capturing a respiratory component of the acoustic signal. The use of the ancillary signals from multiple parameters to assist in the capturing of the respiratory component of the acoustic signal can lead to increased confidence in the accuracy of the respiratory rate measurement, thereby increasing the accuracy, reliability, and effectiveness of the alarm based on the respiratory rate measurement from the acoustic signal.

The display 801B of FIG. 8B includes the same parameter data as the display 801A. However, the display 801B includes a multiparameter confidence indicator 814B that indicates the current multiparameter confidence level numerically, rather than textually (displayed as a percentage in the depicted embodiment). A present multiparameter confidence of 90% is shown by the multiparameter confidence indicator 814B.

The display 800C of FIG. 8C includes a respiratory rate trend graph 816, which depicts respiratory rate measurements over a period of time. The display 801C also depicts a multiparameter confidence indicator 814C in the form of a bar graph below the trend graph 816. The multiparameter confidence indicator 814C includes bars that can correspond to occurrences of breaths of a patient. The bars can have a height that corresponds to a degree of multiparameter confidence in the respiratory rate measurements for any given breath. As the breaths change over time, the multiparameter confidence can also change over time, resulting in a changing multiparameter confidence indicator 814C. The multiparameter confidence indicator 814C can be generated using analogous techniques to those described in the '427 patent described above.

In certain embodiments, the bars can all be depicted with the same color and/or pattern or with varying colors and/or patterns depending on the multiparameter confidence level. For example, bars within a desired multiparameter confidence range can be displayed with a first color and/or pattern, bars within a tolerable multiparameter confidence range can be displayed with a second color and/or pattern, and bars within a low multiparameter confidence range can be displayed with a third color and/or pattern. In certain embodiments, the bars can be replaced with pulses, lines, or other shapes.

Figure 8D:
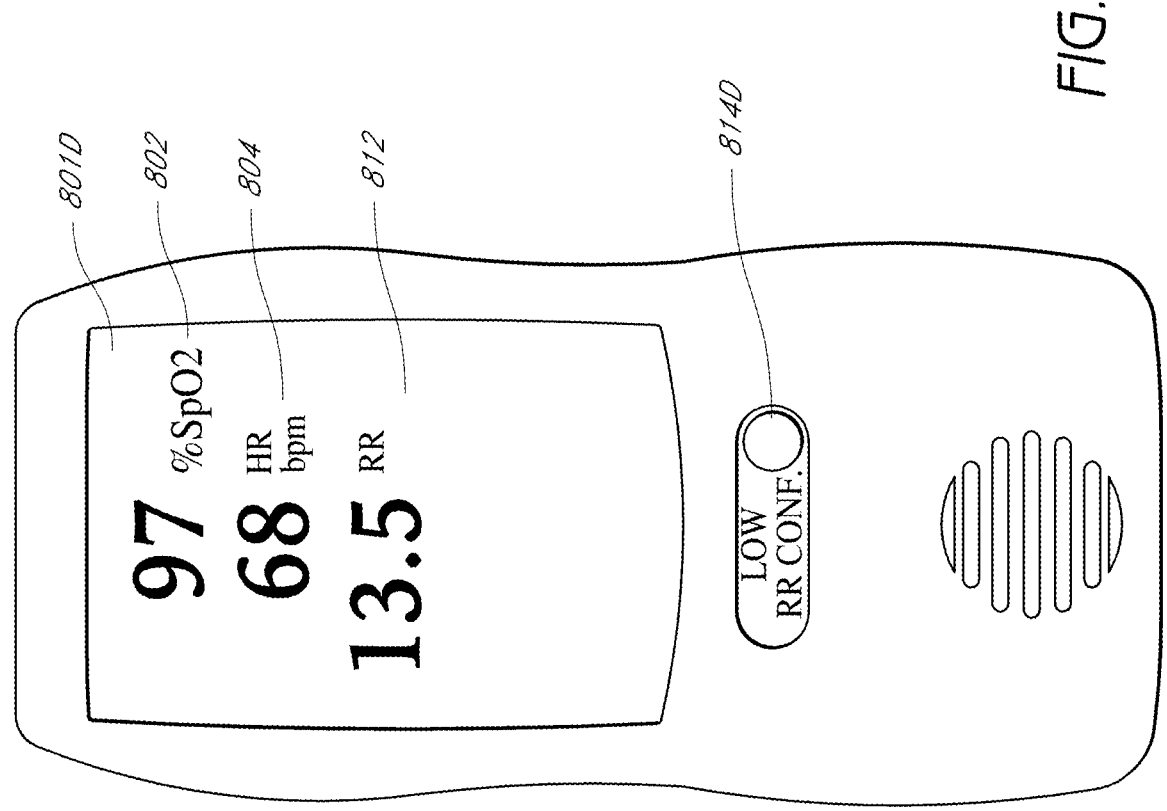

FIG. 8D illustrates another example multiparameter physiological monitor 800 having a display 801D. As shown, the physiological monitor 800 can be configured with a vertical display instead of a horizontal display. The display 801D can include similar parameter data as shown in displays 801A-801C. The multiparameter physiological monitor 800 includes a multiparameter confidence indicator 814D that is positioned off the display 801D. The multiparameter confidence indicator 814D can include one or more light emitting diodes (LEDs) positioned adjacent to text, such as "LOW RR CONF" or "LOW SQ" or "LOW SIQ™," where SQ and SIQ stand for signal quality and signal intelligence quotient, respectively. The multiparameter confidence indicator 810D can be activated to inform a caregiver that a measured value of the multiparameter confidence of the incoming signal is below a certain threshold, for instance. In certain embodiments, different colored LEDs can be used to represent different multiparameter confidence range levels, such as in the manner described above.

The example displays 801A-801D in FIGS. 8A-8D are merely illustrative examples. Many other variations and combinations of multiparameter confidence indicators 814 are also possible in other implementations without departing from the spirit and/or scope of the disclosure.

Moreover, in certain embodiments, the features described in U.S. Pat. No. 6,129,675, filed Sep. 11, 1998 and issued Oct. 10, 2000 and in U.S. patent application Ser. No. 11/899,512, filed Sep. 6, 2007, titled "Devices and Methods for Measuring Pulsus Paradoxus," each of which is hereby incorporated by reference in its entirety, can be used in combination with the features described in the embodiments herein.

Figure 9:
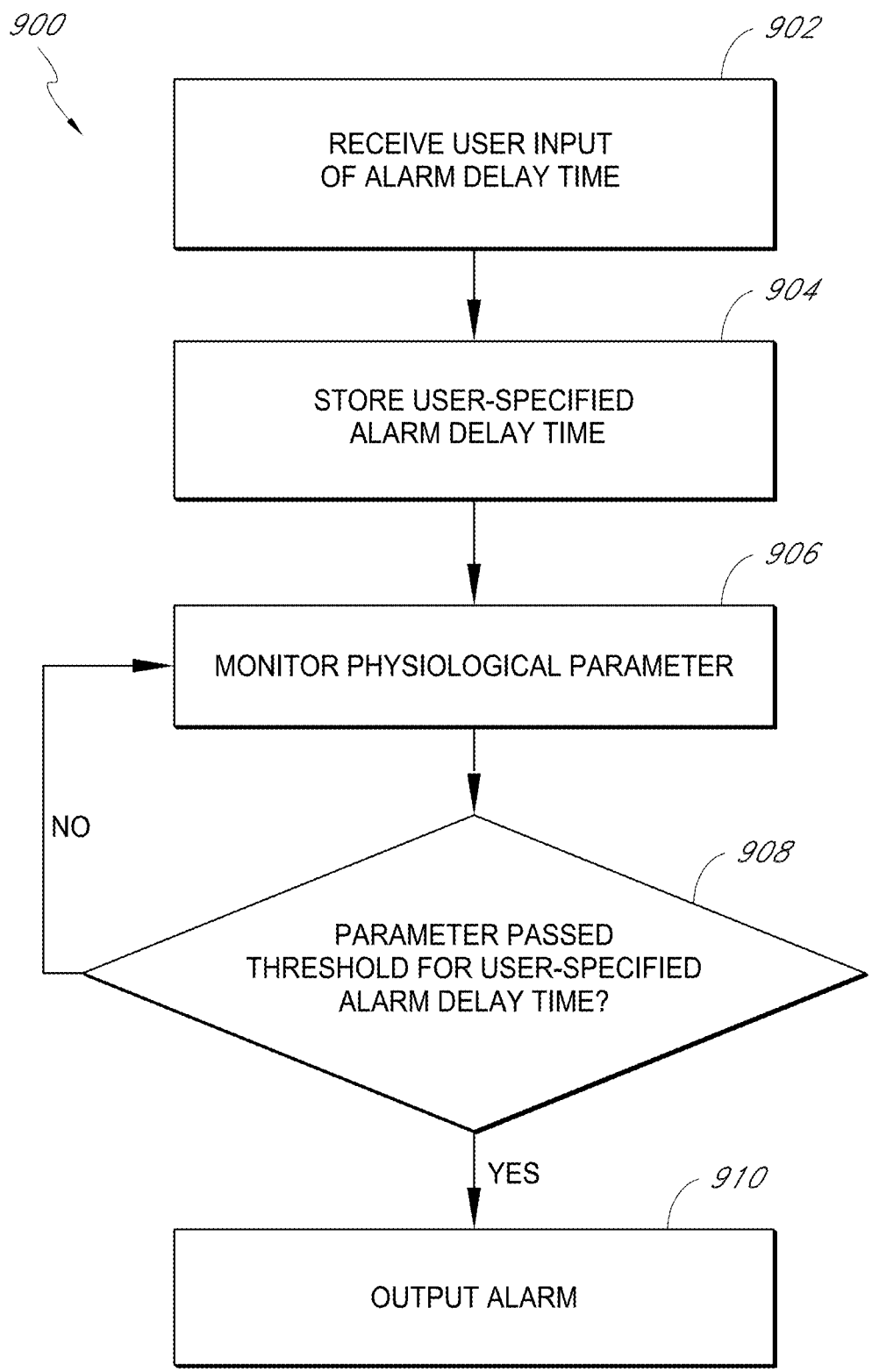
FIG. 9 illustrates an embodiment of a patient monitoring process in which a user can specify a delay time for an alarm to be triggered.

FIG. 9 illustrates an embodiment of a patient monitoring process 900 in which a user (e.g., a clinician) has the ability to specify a delay time for an alarm to be triggered. In one implementation, the patient monitoring process 900 is performed by any of the patient monitoring systems (e.g., systems 10, 200, 400, 500, 600a, 600b) and/or the patient monitors (e.g., monitors 205, 405, 505, 700, 800) described above. More generally, the patient monitoring process 900 can be implemented by a machine having one or more processors. Advantageously, in certain embodiments, the patient monitoring process 900 provides a user-customizable alarm delay that can reduce nuisance alarms.

Currently available patient monitoring devices often generate alarms prematurely or generate alarms that may not correspond to a clinically significant event. For example, a monitoring device can generate an alarm even though the patient's physiological state or condition does not warrant attention. Instead of providing useful, actionable information, these "nuisance" alarms can result in unnecessary worry or stress of the patient and/or clinician and wasted time on the part of the clinician in responding to the nuisance alarms. The patient monitoring process 900 can advantageously reduce or suppress the number of nuisance alarms by providing an alarm delay period. The alarm delay period can advantageously be adjusted by a user.

The patient monitoring process 900 begins by receiving user input of an alarm delay time at block 902. For example, a user such as a clinician can select a desired alarm delay by inputting the desired delay time into a physiological monitor via a user interface, a numerical keypad, or the like. The alarm delay time can correspond to a particular physiological parameter to be monitored. The physiological parameter can include, for example, blood pressure, respiratory rate, oxygen saturation ($SpO_2$) level, other blood constitutions and combinations of constitutions, and pulse, among others. The input from the clinician can adjust a default alarm delay. For example, the default alarm delay time might be 15 seconds, and the clinician input can change the alarm delay time to 30 seconds.

At block 904, the user-specified alarm delay time is stored in a memory device. At block 906, the physiological parameter corresponding to the user-specified alarm delay time is monitored by a patient monitor of a patient monitoring system. At decision block 908, t is determined whether a value of the monitored physiological parameter has remained past a threshold (e.g., above or below a threshold or thresholds) for the user-specified alarm delay time. If it is determined that the value of the monitored physiological parameter has passed a threshold for the time period of the user-specified alarm delay, an alarm is output at block 910. If, however, it is determined that the value of the monitored physiological parameter has not remained past the threshold for the time period of the user-specified alarm delay, the patient monitoring process 900 loops back to block 906 to continue monitoring. In various implementations, the threshold can be set or adjusted by a user (e.g., a clinician) depending on patient-specific factors (e.g., age, gender, comorbidity, or the like).

The alarm can be provided as a visual and/or audible alarm. In one embodiment, the alarm is output by a patient monitor. In another embodiment, the patient monitor transmits the alarm to another device, such as a computer at a central nurses' station, a clinician's end user device (e.g., a pod, a pager), or the like, which can be located in a hospital or at a remote location. The patient monitor can transmit the alarm over a network, such as a LAN, a WAN, or the Internet.

As one example, a user can set an alarm delay time for a respiratory rate to be sixty seconds. In certain situations, a respiratory rate that is outside a threshold range of values for less than sixty seconds can be considered an apnea event. Accordingly, an alarm generated before the respiratory rate has remained outside the threshold range of values for a time period of more than sixty seconds may not be desirable or provide useful information for a clinician to act on. In one embodiment, the patient monitor can monitor the respiratory rate by receiving signals from an acoustic sensor, such as any of the acoustic sensors described herein. When the patient monitor determines that the respiratory rate has been outside a threshold range of values for at least sixty seconds, then an alarm can be output by the patient monitor.

In certain embodiments, an indication can be provided to a user (e.g., a clinician) regarding a current status of the alarm delay period. The indication can be audible and/or visual. In one embodiment, a confidence indicator can be altered or modified based on the alarm delay period. For example, the confidence indicator can be modified to reflect a "countdown" to the time of triggering of the alarm. If the confidence indicator is represented by an LED, for example, the LED can blink once the alarm delay has been initiated and can blink faster as the trigger time of the alarm grows closer. If the confidence indicator is represented by a bar graph, for example, the bars can be modified during the period from initiation of the alarm delay until the time of triggering of the alarm. A separate countdown timer that is not coupled with the confidence indicator could also be provided, which counts down seconds remaining in the alarm delay period.

Figure 10:
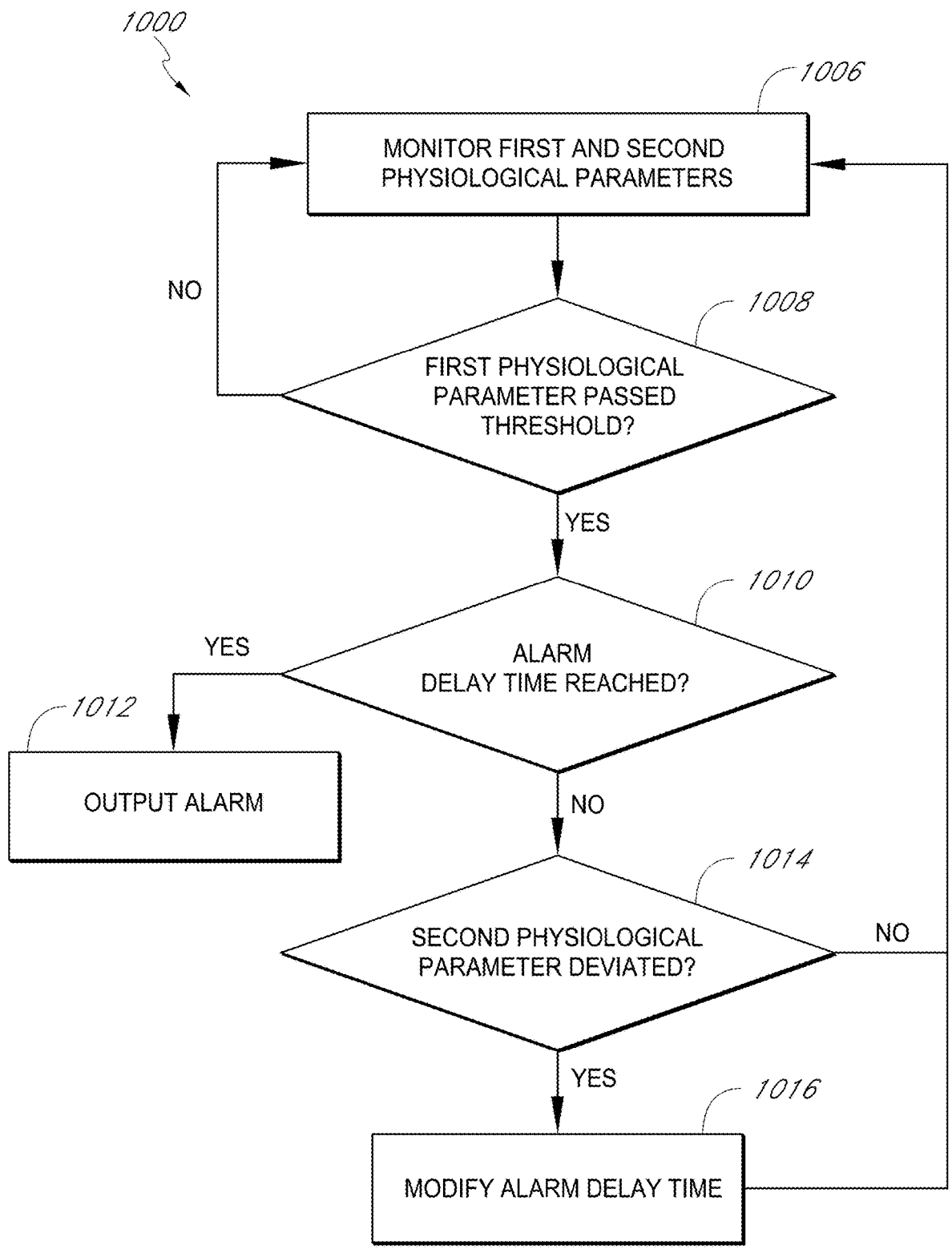
FIG. 10 illustrates an embodiment of a multiparameter patient monitoring process that allows for dynamic modification of an alarm delay.

FIG. 10 illustrates an embodiment of a multiparameter patient monitoring process 1000. In the multiparameter patient monitoring process 1000, an alarm delay time for a first physiological parameter can be modified dynamically based on a measurement of a second physiological parameter. In one implementation, the patient monitoring process 1000 is performed by any of the patient monitoring systems (e.g., systems 10, 200, 400, 500, 600a, 600b) and/or the patient monitors (e.g., monitors 205, 405, 505, 700, 800) described above. More generally, the patient monitoring process 1000 can be implemented by a machine having one or more processors.

At block 1006, first and second physiological parameters are monitored by a multiparameter patient monitor. In one embodiment, respiratory rate and $SpO_2$ are the two monitored physiological parameters. In other embodiments, the first and second monitored physiological parameters can include, for example, blood pressure, respiratory rate, oxygen saturation ($SpO_2$) level, other blood constitutions and combinations of constitutions, and pulse, among others.

At decision block 1008, it is determined whether the current monitored value of the first physiological parameter has passed a threshold. If so, then at decision block 1010, it is determined whether an alarm delay time corresponding to the first parameter has been reached. The alarm delay time can be a default alarm delay time or a user-selected delay time, such as the user-selected delay time described above with respect to FIG. 9. If the first physiological parameter has not passed the threshold, the multiparameter patient monitoring process 1000 loops back to block 1006 to continue monitoring.

If it is determined at decision block 1010 that the user-specified alarm delay time has been reached, then an alarm is output at block 1012. If, however, it is determined that the alarm delay time has not been reached, then the multiparameter patient monitoring process 1000 proceeds to decision block 1014. The alarm can have similar features as described above and can be provided by, on, or to any of the devices described above.

At decision block 1014, it is determined whether a value of the second monitored physiological parameter has deviated from a previous value. If so, then the alarm delay time is dynamically modified at block 1016, and the process 1000 loops back to block 1006 to continue monitoring. If not, the process 1000 loops back to decision block 1006 to continue monitoring without changing the delay time.

In certain embodiments, a deviation from a previous value for the second monitored physiological parameter includes a reduction or increase in value. In other embodiments, a deviation from a previous value includes a deviation beyond a threshold or threshold range of acceptable values. The threshold or threshold range for the second monitored physiological parameter can be set or adjusted by a user (e.g., a clinician) depending on patient-specific factors (e.g., age, gender, comorbidity, or the like). The threshold range of values can be set to include any range of values.

In one embodiment, the degree of modification of the alarm delay can depend on the degree of deviation of the second monitored physiological parameter. In another embodiment, the degree of modification of the alarm delay can also depend on the value of the user-specified or default alarm delay time and/or the identity of the first physiological parameter being monitored.

The dynamic modification can be performed in a linear, step-wise, logarithmic, proportional, or any other fashion. For example, the change in the alarm delay corresponding to the first monitored physiological parameter can be proportional to the change or deviation in the second monitored physiological parameter. In another embodiment, a series of successive threshold ranges of values of the second physiological parameter can be provided, wherein each threshold range corresponds to a different amount of delay adjustment.

For example and not by way of limitation, the first physiological parameter can be respiratory rate and the second physiological parameter can be $SpO_2$. In one embodiment, a user-specified or default alarm delay time can be sixty seconds. If the respiratory rate is less than a given threshold for less than the alarm delay time, it can be determined whether the current $SpO_2$ level has deviated. Based at least partly on this deviation, the alarm delay time can be adjusted. For example, if the $SpO_2$ level has dropped, the alarm delay time can be reduced, for example, to 30 seconds, or to 15 seconds, or to another value. If the second monitored physiological parameter deviates too far beyond a threshold range, an alarm corresponding to the second monitored physiological parameter can also be triggered.

FIGS. 11 through 17 illustrate additional example embodiments of physiological parameter displays 1100-1700. These displays 1100-1700 can be implemented by any physiological monitor, including any of the monitors described herein. The displays 1100-1700 shown illustrate example techniques for depicting parameter values and associated confidence. The displays 1100-1700 can be used to depict single parameter (e.g., internal) confidence, multiparameter confidence, or both. The displays 1100-1700 can be implemented for respiratory rate or for any other physiological parameter, including, but not limited to, $SpO_2$, hemoglobin species (including total hemoglobin), pulse rate, glucose, or any of the other parameters described herein.

Figure 11:
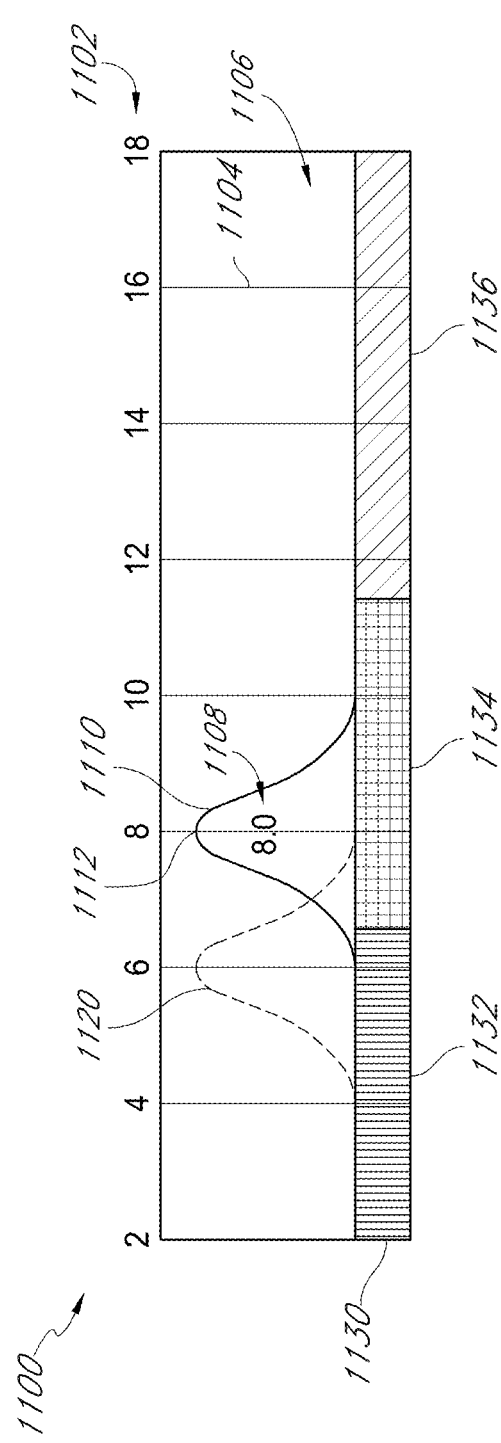

Referring initially to FIG. 11, the display 1100 includes an example parameter value scale 1102 and a plot area 1106. An indicator 1110 displayed in the plot area 1106 plots a parameter value 1108 together with associated confidence. In the depicted embodiment, the indicator 1110 is a normal or Gaussian density function (e.g., bell curve) that includes a peak 1112. The indicator 1110 can represent a current (or most recent) parameter value at the peak 1112 and the confidence associated with that parameter value.

The value of the parameter at the peak 1112 matches the parameter value scale 1102. Thus, for instance, the normal density function is centered at 8.0, and a superimposed value 1108 of "8.0" is superimposed on the indicator 1110, indicating a value of 8.0 for the measured parameter. If the parameter is respiratory rate, the 8.0 can correspond to 8 breaths per minute. If the parameter were hemoglobin (SpHb), the value can be reported as a concentration in g/dL (grams per deciliter) or the like. Other parameters, such as glucose or $SpO_2$, can have different parameter value scales. The parameter value scale 1102 and/or the superimposed value 108 are optional and may be omitted in certain embodiments. Likewise, vertical grid lines 1104 are shown but can be optional, and horizontal grid lines can also be provided.

The confidence is represented in certain embodiments by the characteristics of the indicator 1110 as a normal density function (or a variation thereof). The normal density function can be plotted using the Gaussian function or bell curve:

$$f(x) = \frac{1}{\sqrt{2\pi\sigma^2}} e^{\frac{(x-\mu)^2}{2\sigma^2}}$$

where parameters $\mu$ and $\sigma^2$ are the mean and variance, respectively. Other related formulas can also be used. In one embodiment, the indicator 1110 can be plotted by assigning $\mu$ to be the parameter value and $\sigma^2$ (or $\sigma$, the standard deviation) to be the computed confidence value (internal, multiparameter, or a combination of the same). Then, the location on the parameter scale 1102 of the indicator 1110 can depend on the value of the parameter ($\mu$), and the width or dispersion of the indicator 1110 can depend on the confidence ($\sigma^2$ or $\sigma$). Thus, with higher confidence, the variance ($\sigma^2$) can be lower, and the curve of the indicator 1110 can be narrower. With lower confidence, the variance can be higher, and the curve of the indicator 1110 can be wider or more dispersed.

The parameter value and/or confidence can have values that are some linear combination of $\mu$ and $\sigma^2$. For instance, the parameter value can be represented as $\alpha\mu$, where a is a real number. Likewise, the confidence value can be represented as $\beta\sigma^2$, where $\beta$ is a real number.

Advantageously, in certain embodiments, the indicator 1110 provides an at-a-glance view of a parameter value and associated confidence. Because the confidence can be represented as the width of the indicator 1110, the indicator 1110 can rapidly convey qualitative as well as quantitative information about confidence to a clinician. Most clinicians may be familiar with the normal density function or its associated distribution and may therefore readily associate the shape of the indicator 1110 with qualitative meaning regarding confidence.

Other features of the display 1100 include a phantom indicator 1120, shown as dashed lines, that represents the previous-calculated parameter and confidence values. The phantom indicator 1120 can be used for the immediately previous values, or multiple phantom indicators 1120 can be used for multiple sets of previous values. A safety zone bar 1130 is also displayed. The safety zone bar 1130 includes three areas—a red zone 1132, a yellow zone 1134, and a green zone 1136, representing unsafe, marginally safe, and safe parameter values, respectively. If the peak 1112 of the indicator 1110 is in the green zone 1132, the value is represented as being safe, and so forth. The colors, including any colors discussed herein, may be outlines instead of solid colors. Further, the colors can be replaced with hatch marks, lines, dots, or any of a variety of other indications to represent different zones of safety.

Some example safety zone ranges for respiratory rate for an adult are as follows. The red, or danger zone 1132 can include about 5 breaths per minute (BPM) or less. A second red zone (see, e.g., FIG. 12) might include about 30 BPM or more. The yellow, or marginally safe zone 1134, can include about 6 BPM to about 10 BPM. A second yellow zone (see, e.g., FIG. 12) can include about 24 BPM to about 30 BPM. The green zone 1336 can include about 11 BPM to about 23 BPM. These ranges are merely examples, however, and can vary considerably depending on, for instance, patient age, gender, comorbidity, medications, current activities (e.g., exercising or sitting), combinations of the same, and the like.

Although the normal density function has been used to illustrate confidence, other indicators in other embodiments can be illustrated using different probability density functions (such as binomial or Poisson functions). Further, the indicator need not be illustrated using a probability density function but can instead be illustrated using one or more boxes, circles, triangles, or other geometric shapes whose width, length, height, or other property changes with changing confidence (see, e.g., FIG. 16). Further, the characteristics of the density function can depend on other factors in addition to or instead of confidence, such as patient comorbidities (other diseases can affect the confidence of the measurement), drugs taken by the patient (which can also affect the confidence), age, gender, combinations of the same, and the like. Further, the parameter value scale 1102 can change depending on the range of the parameter being considered, and a clinician can optionally zoom in or zoom out to a smaller or larger range.

Moreover, the safety ranges on the safety zone bar 1130 can depend on or otherwise be adjusted by a clinician based on patient comorbidity (e.g., hemoglobinopathy or thalacemia can affect the safe zones for hemoglobin), medications, age, gender, current activities or patient condition (such as donating blood, which can result in a higher start point of the green safety zone for hemoglobin), combinations of the same, and the like. The alternative implementations described with respect to FIG. 11, as well as any of the other features of the display 1100, can be used for any of the displays 1200-1700 described below as well.

Figure 12:

A variant of the display 1100 is shown as the display 1200 in FIG. 12. The display 1200 also shows an indicator 1210, which can represent a normal density function as described above with respect to FIG. 11. As such, the indicator 1210 can represent a parameter value at a peak of the indicator 1210 and a confidence value associated with the shape of the indicator. In this indicator 1210, however, the indicator 1210 itself is colored to show vertical safety zones 1240, 1242, and 1244. These safety zones can be similar to the safety zones described above with respect to the safety zone bar 1130 of FIG. 11.

The safety zone 1240 can represent a green or safe zone, the safety zone 1242 can represent a yellow or marginal zone, and the zone 1244 can represent a red or danger zone.

Although the indicator 1210 is centered on these zones, different values of the parameter represented by the indicator 1210 can shift the indicator 1210 closer toward one or more of the zones. Thus, the color of the indicator 1210 can change, for example, be entirely yellow, or entirely red, or entirely green, or some different combination of the same. Further, the display 1200 can be modified in some embodiments to add a safety zone bar like the safety zone bar 1130 of FIG. 11. The colors of the safety zone bar can vertically match the colors above the bar shown in the indicator 1210 (see, e.g., FIG. 14).

Figure 13:
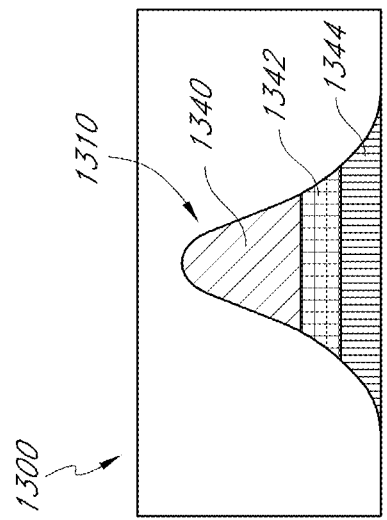

FIG. 13 depicts another embodiment of a display 1300. Similar to the displays 1100, 1200, the display 1300 includes an indicator 1310 that uses normal density function features to represent a parameter value and confidence. However, the indicator 1310 includes horizontal safety zones 1340, 1342, 1344. The horizontal zones can be similar to the safety zones described above and can include, for example, red, green, and yellow (or other) colors. In another embodiment (not shown), the indicator 1310 can be a single solid color corresponding to the safety zone of the peak of the indicator 1310. The indicator 1310 can also include gradual instead of abrupt transitions between colors.

Referring to FIG. 14, a display 1400 includes an indicator 1410 having the density function characteristics described above. In addition, the indicator 1410 is colored vertically with safety zones 1442 and 1444, similar to the indicator 1210 above. In addition, a safety zone bar 1430 is also shown, which has colors that correspond vertically to the colors of the indicator 1410. Thus, a zone 1440 can be green, the zones 1442 and 1452 (of the bar 1430) can be yellow, and the zones 1444 and 1454 (of the bar) can be red, or the like.

FIG. 15 illustrates a display 1500 having an indicator 1510 without color. Instead, the indicator 1510, which can include the features of the indicators described above, includes markings 1520 to reflect percentages of standard deviations of the normal density function. These standard deviations can correspond to confidence intervals. These markings 1520 include horizontal arrows, vertical lines, and associated percentage numbers to mark a first standard deviation (e.g., 68% confidence that the parameter lies within the interval marked by the arrow), a second standard deviation (e.g., 95% confidence that the parameter lies within the interval marked by the arrow), and the third standard deviation (e.g., 99% confidence interval). Color or safety zones can be added to the indicator 1510 as in any of the other example indicators described herein.

FIG. 16 illustrates yet another display 1600 with an indicator 1600. Unlike the indicators described above, the indicator 1610 is not a bell curve but instead a geometric arrangement of vertical bars 1612. The vertical bars 1612 can approximate a bell curve, however. Horizontal bars may also be used similarly. The width of the vertical bars 1612 and/or the width of the indicator 1600 as a whole can represent the confidence of a parameter. Further, the parameter value can be represented by the center bar 1612 on a parameter value scale (not shown; see FIG. 11). The narrower the indicator 1610, the more confidence is represented, and the wider the indicator 1610, the less confidence is represented, in one embodiment.

Figure 17:
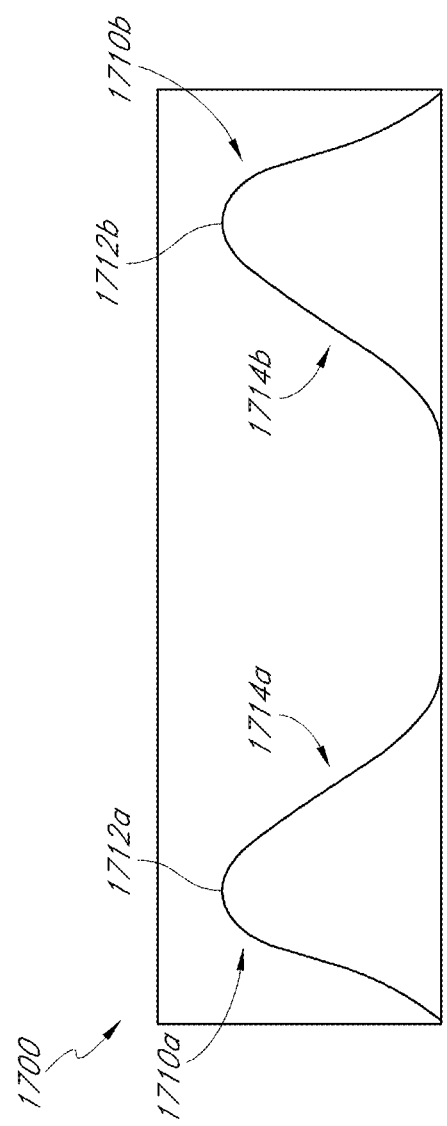

Referring to FIG. 17, another embodiment of a display 1700 is shown. The display 1700 illustrates additional features that can be combined with any of the embodiments described above. The display 1700 includes two indicators 1710*a*, 1710*b*. Each of the indicators 1710 is asymmetrical instead of bell-curve shaped. On one side of the peak 1712*a*, 1712*b* for each indicator 1710*a*, 1710*b*, a portion 1714*a*, 1714*b* of the curve is wider or more dispersed than the other side, leading to the asymmetry.

In one embodiment, the indicator 1710 can be asymmetrical if the confidence measure indicates higher confidence on one side of the parameter value as opposed to the other. Asymmetric confidence can occur for some parameters due to bias. For instance, with hemoglobin, a bias for more positive values at lower values of hemoglobin may occur based on the levels of other blood constituents such as oxygen saturation ($SpO_2$) or carboxyhemoglobin (SpCO). Similarly, hemoglobin can have a bias for more negative values at higher values of hemoglobin based on levels of other blood constituents. Thus, for lower values of hemoglobin, the curve may be wider in the positive direction, and vice versa.

Positive asymmetry for lower parameter values is illustrated by the indicator 1710*a*, while negative asymmetry for higher parameter values is illustrated by the indicator 1710*b*. To illustrate both positive and negative asymmetry, two indicators 1710*a*, 1710*b* are depicted on the display 1700. However, in one implementation, only one indicator 1710 is displayed. Multiple indicators are also possible, such as for multiple parameters on a single display. Moreover, the features described herein with respect to FIG. 17 can be extended to arbitrary geometric shapes. A triangle, for instance, can have one half that is wider than another half based on positive or negative bias in confidence levels.

Any of the displays 1100-1700 can be used to indicate the occurrence and/or severity of an alarm. For instance, the indicators described above can pulsate or flash when an alarm occurs, optionally in conjunction with an audible alarm. The seriousness of the alarm can depend at least partially on the measured confidence. Higher confidence (e.g., a narrow indicator) can result in a more urgent alarm, whereas less urgent alarms can result for less confident parameter values. This urgency can be displayed in a variety of ways, for example, by increasing the rate that the indicator flashes, increasing the frequency and/or pitch of an audible alarm, combinations of the same, and the like.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A system for monitoring a respiratory rate measurement from a patient, the system comprising:
    one or more hardware processors configured to:
        receive an acoustic signal generated by an acoustic sensor responsive to vibrations of a patient,
        determine, from the acoustic signal, a first measurement of a respiratory rate,
        determine a first range of measurements of the respiratory rate from one or more characteristics of the patient, the first range of measurements forming a first safety zone, and
        determine a second range of measurements of the respiratory rate from the one or more characteristics, the second range of measurements forming a second safety zone, the second range of measurements being different from the first range of measurements and representing a greater safety risk to the patient than the first range of measurements; and
    a display configured to present the first safety zone and the second safety zone together with an indicator, the indicator being positioned according to the first measurement, a position of the indictor relative to the first safety zone and the second safety zone denoting whether the first measurement is within the first range of measurements or the second range of measurements and denoting a degree of safety concern for the patient estimated from the first measurement.

2. The system of claim 1, wherein
when at least one of the one or more characteristics has a first magnitude, the display is configured to present the indicator so that the position of the indicator denotes that the first measurement is within the first range of measurements and denotes that the degree of safety concern is less than if the first measurement were within the second range of measurements, and
when at least one of the one or more characteristics has a second magnitude different from the first magnitude, the display is configured to present the indicator so that the position of the indicator denotes that the first measurement is within the second range of measurements and denotes that the degree of safety concern is greater than if the first measurement were within the first range of measurements.

3. The system of claim 1, wherein
when at least one of the one or more characteristics is within a first category, the display is configured to present the indicator so that the position of the indicator denotes that the first measurement is within the first range of measurements and denotes that the degree of safety concern is less than if the first measurement were within the second range of measurements, and
when at least one of the one or more characteristics is within a second category different from the first category, the display is configured to present the indicator so that the position of the indicator denotes that the first measurement is within the second range of measurements and denotes that the degree of safety concern is greater than if the first measurement were within the first range of measurements.

4. The system of claim 1, wherein the one or more characteristics comprises a comorbidity for the patient.

5. The system of claim 1, wherein the one or more characteristics comprises a medication being used by the patient.

6. The system of claim 1, wherein the one or more characteristics comprises an age of the patient.

7. The system of claim 1, wherein the one or more characteristics comprises a gender of the patient.

8. The system of claim 1, wherein the one or more characteristics comprises an activity engaged in by the patient.

9. The system of claim 1, wherein
the one or more hardware processors is configured to determine a third range of measurements of the respiratory rate from the one or more characteristics, the third range of measurements forming a third safety zone, the third range of measurements being different from the first range of measurements and the second range of measurements, the third range of measurements representing a greater safety risk to the patient than the second range of measurements; and the display is configured to present the first safety zone, the second safety zone, and the third safety zone together with the indicator, the position of the indictor relative to the first safety zone, the second safety zone, and the third safety zone denoting whether the first measurement is within the first range of measurements, the second range of measurements, or the third range of measurements and denoting the degree of safety concern for the patient estimated from the first measurement.

10. The system of claim 1, wherein
the one or more hardware processors is configured to determine, from the acoustic signal, a second measurement of the respiratory rate, the second measurement being different from the first measurement; and the display is configured to reposition the indicator according to the second measurement so that the position of the indicator relative to the first safety zone and the second safety zone denotes whether the second measurement is within the first range of measurements or the second range of measurements and denotes the degree of safety concern for the patient estimated from the second measurement.

11. The system of claim 1, wherein the one or more hardware processors is configured to activate an alarm responsive to the first measurement being within the first range of measurements.

12. The system of claim 1, wherein the one or more hardware processors is configured to change the one or more characteristics responsive to a user input.

13. The system of claim 1, wherein the display is configured to present the first safety zone in a first color and the second safety zone in a second color different from the first color.

14. The system of claim 1, wherein the display is configured to present a numerical value of the first measurement together with the first safety zone, the second safety zone, and the indicator.

15. A method for monitoring a respiratory rate measurement from a patient, the method comprising:
receiving, by one or more hardware processors, an acoustic signal generated by an acoustic sensor responsive to vibrations of a patient;
determining, by the one or more hardware processors from the acoustic signal, a first measurement of a respiratory rate;
determining, by the one or more hardware processors, a first range of measurements of the respiratory rate from one or more characteristics of the patient, the first range of measurements forming a first safety zone;
determining, by the one or more hardware processors, a second range of measurements of the respiratory rate from the one or more characteristics, the second range of measurements forming a second safety zone, the second range of measurements being different from the first range of measurements and representing a greater safety risk to the patient than the first range of measurements; and
presenting, by a display, the first safety zone and the second safety zone together with an indicator, the indicator being positioned according to the first measurement, a position of the indictor relative to the first safety zone and the second safety zone denoting whether the first measurement is within the first range of measurements or the second range of measurements and denoting a degree of safety concern for the patient estimated from the first measurement.

16. The method of claim 15, wherein said presenting comprises presenting the indicator so that the position of the indicator denotes that the first measurement is within the first range of measurements and denotes that the degree of safety concern is less than if the first measurement were within the second range of measurements, and further comprising:
changing the one or more characteristics to obtain a changed one or more characteristics;
determining, by the one or more hardware processors from the acoustic signal, a second measurement of the respiratory rate, the second measurement being the same as the first measurement;
adjusting, by the one or more hardware processors, the first range of measurements according to the changed one or more characteristics to obtain an adjusted first range of measurements that forms an adjusted first safety zone;
adjusting, by the one or more hardware processors, the second range of measurements according to the changed one or more characteristics to obtain an adjusted second range of measurements that forms an adjusted second safety zone; and
presenting, by the display, the adjusted first safety zone and the adjusted second safety zone together with the indicator positioned according to the second measurement so that the position of the indictor relative to the adjusted first safety zone and the adjusted second safety zone denotes that the second measurement is within the adjusted second range of measurements and denotes that the degree of safety concern is greater than if the second measurement were within the adjusted first range of measurements.

17. The method of claim 15, wherein the one or more characteristics comprises two or more of: a comorbidity for the patient, a medication being used by the patient, an age of the patient, a gender of the patient, or an activity engaged in by the patient.

18. The method of claim 15, further comprising determining, by the one or more hardware processors, a third range of measurements of the respiratory rate from the one or more characteristics, the third range of measurements forming a third safety zone, the third range of measurements being different from the first range of measurements and the second range of measurements, the third range of measurements representing a greater safety risk to the patient than the second range of measurements,
wherein said presenting comprises presenting, by the display, the first safety zone, the second safety zone, and the third safety zone together with the indicator, the position of the indictor relative to the first safety zone, the second safety zone, and the third safety zone denoting whether the first measurement is within the first range of measurements, the second range of measurements, or the third range of measurements and denoting the degree of safety concern for the patient estimated from the first measurement.

19. The method of claim 15, further comprising activating, by the one or more hardware processors, an alarm in response to the first measurement being within the first range of measurements.

20. The method of claim 15, further comprising changing, by the one or more hardware processors, the one or more characteristics in response to a user input.

* * * * *

UNITED STATES PATENT AND TRADEMARK OFFICE
CERTIFICATE OF CORRECTION

| | | |
|---|---|---|
| PATENT NO. | : 10,813,598 B2 | Page 1 of 2 |
| APPLICATION NO. | : 15/851176 | |
| DATED | : October 27, 2020 | |
| INVENTOR(S) | : Al-Ali et al. | |

It is certified that error appears in the above-identified patent and that said Letters Patent is hereby corrected as shown below:

In the Drawings

Drawing Sheet 10 of 22, FIG. 6B-1, Line 5, delete "Photpleth" and insert --Photopleth--.

Drawing Sheet 12 of 22, FIG. 6C, Line 5, delete "Photpleth" and insert --Photopleth--.

In the Specification

Column 2, Line 50, delete "disclosure;" and insert --disclosure.--.

Column 2, Line 53, delete "disclosure;" and insert --disclosure.--.

Column 7, Line 62, delete "etc)," and insert --etc.),--.

Column 22, Line 47, delete "t" and insert --it--.

Column 25, Line 21, delete "108" and insert --1108--.

Column 25, Line 51, delete "a" and insert --α--.

In the Claims

Column 30, Line 15, Claim 1, delete "indictor" and insert --indicator--.

Column 31, Line 10, Claim 9, delete "indictor" and insert --indicator--.

Column 32, Line 2, Claim 15, delete "indictor" and insert --indicator--.

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,813,598 B2

Column 32, Line 35, Claim 16, delete "indictor" and insert --indicator--.

Column 32, Line 61, Claim 18, delete "indictor" and insert --indicator--.